(12) United States Patent
Ikeda et al.

(10) Patent No.: US 8,164,828 B2
(45) Date of Patent: Apr. 24, 2012

(54) OBSERVABLE CENTRIFUGAL APPARATUS AND OBSERVATION APPARATUS

(75) Inventors: Norifumi Ikeda, Fujisawa (JP); Nobuaki Tanaka, Fujisawa (JP); Koichi Morita, Fujisawa (JP)

(73) Assignee: NSK Ltd., Tokyo (JP)

( * ) Notice: Subject to any disclaimer, the term of this patent is extended or adjusted under 35 U.S.C. 154(b) by 457 days.

(21) Appl. No.: 12/520,092

(22) PCT Filed: Nov. 19, 2007

(86) PCT No.: PCT/JP2007/072369
§ 371 (c)(1),
(2), (4) Date: Jun. 18, 2009

(87) PCT Pub. No.: WO2008/078475
PCT Pub. Date: Jul. 3, 2008

(65) Prior Publication Data
US 2010/0027110 A1 Feb. 4, 2010

(30) Foreign Application Priority Data

Dec. 26, 2006 (JP) ................................ 2006-349612
Jun. 29, 2007 (JP) ................................ 2007-171766

(51) Int. Cl.
*G02B 21/00* (2006.01)
*B04B 15/00* (2006.01)
(52) U.S. Cl. ........................................ 359/368; 494/10
(58) Field of Classification Search .................. 359/368, 359/390, 394; 356/72; 362/253; 494/10
See application file for complete search history.

(56) References Cited

U.S. PATENT DOCUMENTS

| 1,907,803 A | * | 5/1933 | Harvey et al. ................. 359/390 |
| 3,009,388 A | * | 11/1961 | Polanyi ........................... 356/40 |
| 5,930,033 A | * | 7/1999 | Inoue et al. .................... 359/368 |

(Continued)

FOREIGN PATENT DOCUMENTS

JP  63-250615 A  10/1988

(Continued)

OTHER PUBLICATIONS

Harvey et al, "A Microscope-Centrifuge," Science, 1930, vol. 72, No. 1854, pp. 42-44.

(Continued)

*Primary Examiner* — Frank Font
(74) *Attorney, Agent, or Firm* — Miles & Stockbridge P.C.

(57) ABSTRACT

Disclosed is an observable centrifugal apparatus capable of checking in real time a state of a sample during reaction of separation or synthesization in the form of a stable and high-quality image at a high frame rate. An observable centrifugal apparatus A has a rotary disc 4 rotating about a rotary shaft 2, a reactor 6 disposed on the rotary disc and rotating together with the rotary disc while accommodating a sample, and a microscope 8 for observing a state of the sample within the reactor, in which predetermined substances of the sample are separated or synthesized by applying a centrifugal force to the sample within the reactor. The microscope is fixed in a predetermined position on the rotary disc so as to enable the state of the sample within the reactor to be observed, and the rotary disc is fitted with an imaging device 19 for photographing the state of the sample, caught by the microscope, within the reactor and a microscope image, and with an image wireless transmission device 12 for wirelessly transmitting in real time the photographed image of the microscope image photographed by the imaging device as a dynamic image.

16 Claims, 16 Drawing Sheets

U.S. PATENT DOCUMENTS

| | | | | |
|---|---|---|---|---|
| 5,982,535 | A | * | 11/1999 | Inoue et al. ............... 359/394 |
| 7,936,501 | B2 | * | 5/2011 | Smith et al. ............... 359/368 |
| 2002/0067543 | A1 | * | 6/2002 | Inou et al. ............... 359/368 |

FOREIGN PATENT DOCUMENTS

| | | | | |
|---|---|---|---|---|
| JP | 63250615 | A | * | 10/1988 |
| JP | 3-39711 | A | | 2/1991 |
| JP | 11-109245 | A | | 4/1999 |
| JP | 11258511 | A | * | 9/1999 |
| JP | 11264716 | A | * | 9/1999 |
| JP | 2003-533682 | A | | 11/2003 |
| JP | 2004-109099 | A | | 4/2004 |
| JP | 2004-118190 | A | | 4/2004 |
| JP | 2004-125773 | A | | 4/2004 |
| JP | 2004-279075 | A | | 10/2004 |
| JP | 2005-509882 | A | | 4/2005 |
| JP | 2006-501805 | A | | 1/2006 |
| JP | 2006-134458 | A | | 5/2006 |
| JP | 2006-297060 | A | | 11/2006 |

OTHER PUBLICATIONS

Friedrich et al., "The slow rotating centrifuge microscope NIZEMI—A versatile instrument for terrestrial hypergravity and space microgravity research in biology and materials science," Journal of Biotechnology, 1996, vol. 47, pp. 225-238.

Hiramoto et al., "Centrifuge Microscope as a Tool in the Study of Cell Motility," International Review of Cytology, 1995, vol. 157, pp. 99-128.

Inoue et al, "Centrifuge polarizing microscope. I. Rationale, design and instrument performance," Journal of Microscopy, Mar. 2001, vol. 201, Pt. 3, pp. 341-356.

Inoue et al, "Centrifuge polarizing microscope. II. Sample biological applications," Journal of Microscopy, Mar. 2001, vol. 201, Pt. 3, pp. 357-367.

Kuroda et al, "Behavior of Cytoplasmic Streaming in Nitella During Centrifugation as Revealed by the Television Centrifuge-Microscope," Biorheology, 1981, vol. 18, pp. 633-641.

Kuroda et al., "Propulsive Force of Paramecium as Revealed by the Video Centrifuge Microscope," Experimental Cell Research, 1989, vol. 184, pp. 268-272.

Baskin, "Design and Use of the Centrifuge Microscope to Assay Force Production," Methods in Enzymology, 1998, vol. 298, pp. 413-427.

Harvey, "Some Physical Properties of Protoplasm," Journal of Applied Physics, Feb. 1938, vol. 9, pp. 68-80.

The Hitotsubashi Review, 1981, vol. 86, pp. 805-813.

Kamitsubo, "Centrifuge Microscope," Biophysical Society of Japan, 1990, vol. 30, No. 5, pp. 52-54.

* cited by examiner

OBSERVABLE CENTRIFUGAL APPARATUS AND OBSERVATION APPARATUS

TECHNICAL FIELD

The present invention relates generally to a centrifugal force apparatus which separates or synthesizes predetermined substances of a sample by applying a centrifugal force to the sample, and more particularly to an observable centrifugal apparatus and an observation apparatus each capable of checking in real time a state of the sample during separating reaction or synthesizing reaction by visually recognizing the state of the sample.

BACKGROUND ART

There have hitherto been known a variety of centrifugal apparatuses (e.g., centrifugal separators) and centrifugal methods for separating or synthesizing predetermined substances (a liquid, a solid body and a gas, or a mixture thereof) of a sample within a reactor by applying a centrifugal force to the sample, and a variety of industrial products and medicines are purified by the centrifugal apparatuses and the centrifugal methods, or impurities are removed from semi-finished products or reagents by the centrifugal apparatuses and the centrifugal methods.

For example, Patent document 1 discloses, by way of one example, a hematology analyzer (a chip-type reactor), in which a blood plasma or a blood serum is separated from the blood and purified on the centrifugal separator, and is mixed with a variety of reagents.

Further, Patent document 2 discloses, by way of one example, a micro system (which includes a centrifugal apparatus and a centrifugal method for performing a micro analysis) for mixing the liquid by utilizing a phenomenon that a flow of the liquid is caused by a centripetal force generated by rotation.

Still further, Patent document 3 discloses, by way of one example, such a rotary type optical bio-disc which treats a blood sample for a clinical diagnosis and is provided with a fluid circuit for measuring, e.g., a blood cell quantity (such as a red blood count and a leukocyte count). The rotary type optical bio-disc such as this is loaded into a predetermined optical reader and rotationally processed only for a predetermined period of time at a predetermined rotating velocity.

Yet further, Patent document 4 discloses, by way of one example, a method for removing negatively-charged minute organic molecules from a biomolecule sample mixture and a rotary disc type reactor (device) used for this method.

Herein, when a separating operation for the sample is performed by use of the rotary type reactor, it is required that the reactor is rotated, and simultaneously a substance migration state within the reactor and a reaction state be observed (checked) during this operation.

Patent document 5 discloses, as one example of the centrifugal apparatus including the observation mechanism described above, an optical system for polarizing observation (an optical mechanism for the polarizing observation,) that includes an objective lens in which a sample chamber (reactor) on the rotary disc is disposed so as to transect the optical axis thereof, and a centrifugal microscope including a light source which emits laser beams to the polarizing observation optical system at timing when the sample chamber transects the optical axis of the objective lens.

[Patent document 1] Japanese Patent Laid-Open Publication No. 2004-109099

[Patent document 2] Japanese Unexamined Patent Publication No. 2003-533682

[Patent document 3] Japanese Unexamined Patent Publication No. 2005-509882

[Patent document 4] Japanese Unexamined Patent Publication No. 2006-501805

[Patent document 5] Japanese Patent Laid-Open Publication No. H11-109245

DISCLOSURE OF THE INVENTION

Problems to be Solved by the Invention

In the centrifugal microscope (the centrifugal apparatus) disclosed in Patent document 5, however, the polarizing observation optical mechanism other than the rotary disc is disposed, and the state of the sample is observed with the aid of the light emitting source which emits the light in synchronization with the rotation of the rotary disc, in which case it follows that only frames corresponding to the rotation of the rotary disc can be observed. Namely, in the case of the centrifugal microscope (the centrifugal apparatus) in which the rotary disc makes one rotation per second, a problem is that an observable limit frame count is one frame per second.

Moreover, when the microscope is disposed on the rotary disc, the centrifugal force is applied to a lens barrel of the microscope, and hence it is difficult to make the stable observation because of an increase in vibrations of the lens barrel, in addition, another problem is that the same centrifugal force on the reactor is applied also to a CCD (Charge Coupled Device) for photographing the image, with the result that the operation of the CCD camera becomes unstable. Further, in this case, it is difficult to connect a cable for outputting the image signals from the rotating CCD camera, and, even when employing a method of obtaining rotational conduction by bringing a brush into contact with a conductive plate as in the case of, e.g., a slip ring, the stable observation might be attained with the difficulty due to image disturbance caused by noises mixed in the image signals.

It is a first object of the present invention, which was devised for solving the problems described above, to provide an observable centrifugal apparatus capable of checking in real time a state of a sample in the process of separating reaction or synthesizing reaction through an image with a stable image quality at a high frame rate (the number of frames).

Further, it is a second object of the present invention to provide an observable centrifugal apparatus and an observation apparatus each capable of further improving magnification and resolution.

Means for Solving the Problems

To accomplish the objects given above, an observable centrifugal apparatus according to the present invention comprises: a rotary disc which rotates; a reactor which is disposed on said rotary disc and rotates together with said rotary disc while housing a sample; and a microscope used for observing a state of the sample within said reactor by visually recognizing the state of the sample, said observable centrifugal apparatus separating or synthesizing predetermined substances from the sample within said reactor by applying a centrifugal force to said sample, wherein said microscope is fixed in a predetermined position of said rotary disc so as to enable a state of the sample within said reactor to be observed, and said rotary disc is fitted with an imaging device for photographing a microscope image of the sample state within said reactor, caught by said microscope, and with an image wireless transmission device for wirelessly transmitting in real time the photographed image of the microscope image photographed by said imaging device as a dynamic image.

In this case, the light path of the microscope is partially, within a lens barrel, refracted at a predetermined angle to a disc surface of the rotary disc, and the imaging device is positioned in the vicinity of the center of rotation of the rotary disc so that the microscope image can be photographed on the light path of the microscope, which is refracted at the predetermined angle. With this configuration, even when the centrifugal force is generated by the rotation of the rotary disc, the centrifugal force applied to the imaging device can be reduced, and the microscope image can be photographed stably at all times by the imaging device.

It should be noted that the rotary shaft of the rotary disc is, it is sufficient, rotatably supported by a variety of bearings, however, the rotating vibrations caused when the rotary disc rotates can be remarkably decreased by rotatably supporting the rotary shaft with an air bearing, and by extension the state of the sample during the separating reaction or the synthesizing reaction can be stably observed and photographed in a way that restrains the rotating vibrations of the microscope and of the imaging device. In this case, the air bearing is kept in a non-contact state with the rotary shaft by dint of blast air.

Moreover, an objective lens of the microscope and the reactor are integrally fixed to the rotary disc through the same component, whereby relative displacement between the objective lens and the reactor due to the rotational vibrations can be minimized.

Further, as one example, the image wireless transmission device converts data of the photographed image of the microscope image photographed by the imaging device into non-compressed digital signals, and wirelessly transmits the digital signals to an external receiving device. With this scheme, the image signals transmitted from the image wireless transmission device can be transmitted to the external receiving device without any loss of the image signals, and the separating reaction or the synthesizing reaction can proceed while checking the state of the sample through the clear and stable image in the receiving device.

Still further, the observable centrifugal apparatus further comprises an epi-illumination apparatus performing epi-illumination over the sample within said reactor, whereby it is feasible to obtain the light and shade (contrast) owing to reflection from the sample surface even when optical transmittance of the sample is substantially the same as the transmittance of the background, and hence a behavior of the sample can be clearly observed.

Yet further, a configuration that the rotary disc is rotationally driven by a direct drive motor enables the observable centrifugal apparatus to be constructed as a motor built-in type apparatus and to be thus downsized.

Yet further, it is preferable that the observable centrifugal apparatus further comprises an illumination apparatus performing backlight illumination over the sample within the reactor. In this case, it is preferable that the observable centrifugal apparatus further comprises a sample fitting portion to which the reactor is fitted, wherein the sample fitting portion includes a sample board which supports the reactor and is formed with a pinhole, and backlight illumination beams emitted from the illumination apparatus penetrate the pinhole and illuminate over the sample within the reactor supported on the sample board. The sample within the reactor is illuminated with the transmitted beams penetrating the pinhole formed in the sample board, thereby leading to an improvement of an image contrast, enabling the image with a high resolution to be acquired and therefore enabling realization of the observable centrifugal apparatus capable of further improving the magnification and the resolution.

Moreover, the sample fitting portion includes an alignment mechanism for adjusting a relative position between an optical axis of the objective lens of the microscope and the pinhole of the sample board, whereby the position of the pinhole of the sample board can be easily aligned with the optical axis of the objective lens.

Additionally, the sample fitting portion includes a sample holder which holds the reactor on the sample board, and a position adjusting mechanism for adjusting a relative position between the optical axis of the objective lens of the microscope and the reactor held by the sample holder, whereby an objective observation region within the reactor can be easily aligned with the optical axis of the objective lens.

Further, it is preferable that the sample fitting portion is provided within a fixation component which fixes the objective lens of the microscope to the rotary disc, and the sample board and the sample holder are fixed on the side of the rotary disc by the alignment mechanism, the position adjusting mechanism and the fixation component.

According to the observable centrifugal apparatus of the present invention, the microscope for observing the internal state of the reactor on the rotary disc is provided, and the imaging device for photographing the microscope image and the image wireless transmission device for wirelessly transmitting in real time the photographed image sent from the imaging device are each fitted in the vicinity of the center of rotation of the rotary disc, whereby the centrifugal force acting on each device can be minimized, and the state of the sample in the reactive process of the separating reaction or the synthesizing reaction can be checked in real time through the image with the stable image quality at the high frame rate (frame count) because of no hindrance against the device performance due to the centrifugal force. Moreover, the sample board for supporting the reactor is formed with the pinhole, and the sample is backlight-illuminated with the transmitted beams penetrating the pinhole, thereby enabling the magnification and the resolution to be further improved.

An observation apparatus according to the present invention comprises: a microscope for observing an observation object; a sample board which supports the observation object; and an illumination apparatus which performs backlight illumination over the observation object, wherein the sample board is formed with a pinhole, and the backlight illumination beams emitted from the illumination apparatus penetrate the pinhole and illuminate over the observation object supported on the sample board.

According to this observation apparatus, the observation object is backlight-illuminated with the transmitted beams penetrating the pinhole formed in the sample board, whereby the image contrast is improved, and the image with the high resolution can be obtained. Therefore, the magnification and the resolution can be further improved.

The observation apparatus further comprises an alignment mechanism for adjusting a relative position between an optical axis of the objective lens of the microscope and the pinhole of the sample board, whereby the position of the pinhole of the sample board can be easily aligned with the optical axis.

Further, the observation apparatus further comprises a position adjusting mechanism for adjusting a relative position between the optical axis of the objective lens of the microscope and the observation object supported on the sample board, whereby the objective observation region of the observation object can be easily aligned with the optical axis of the objective lens.

Figure 1:
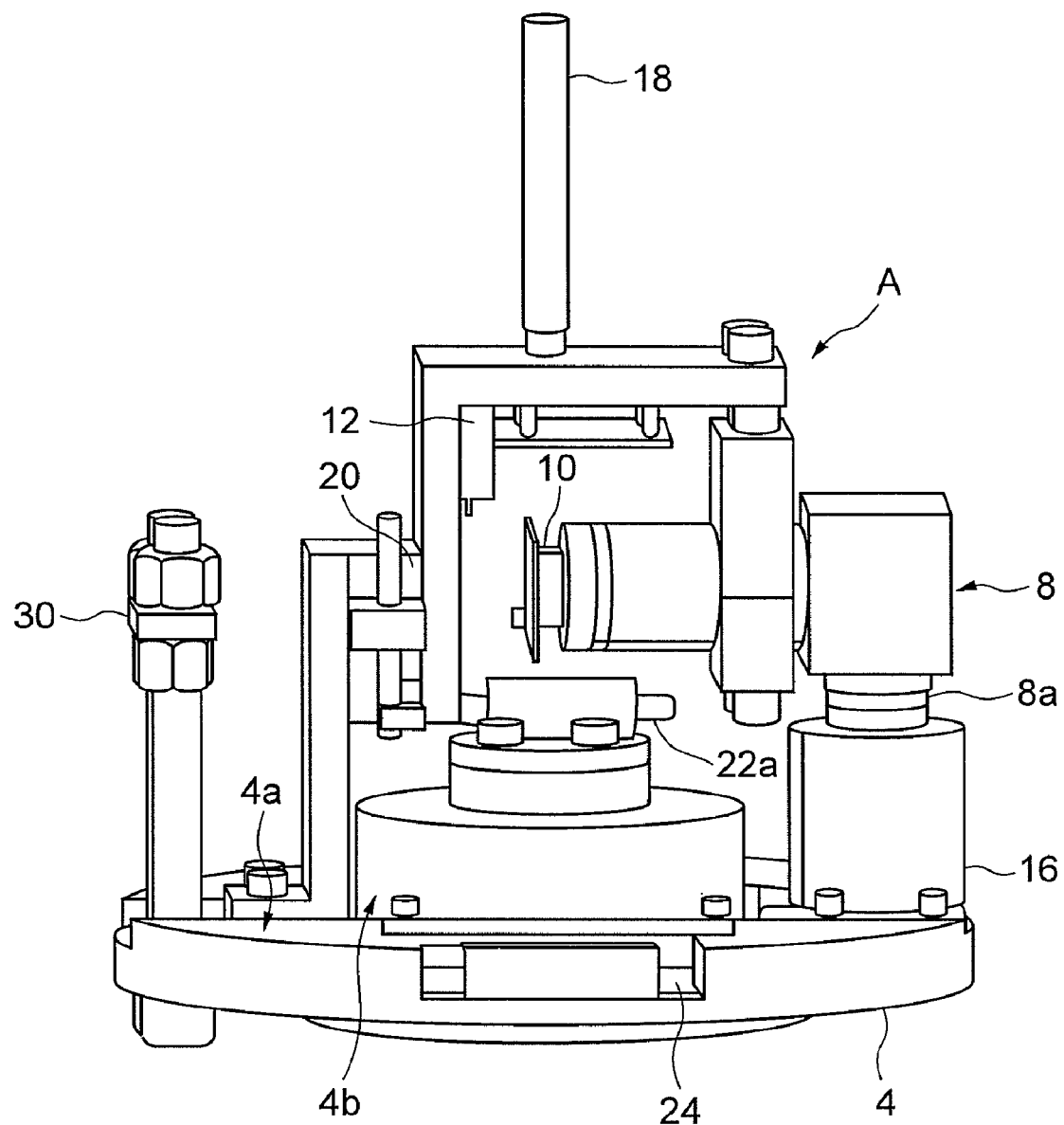
[FIG. 1] A perspective view illustrating an example of a whole configuration of an observable centrifugal apparatus according to a first embodiment.

BRIEF DESCRIPTION OF THE REFERENCE NUMERALS AND SYMBOLS 2 rotary shaft
4 rotary disc
6 reactor
8 microscope
8a objective lens
10 imaging device
12 image wireless transmission device
14 mirror
14a half-mirror
16 fixation component
18 antenna
20 Z-axis guide
22 illumination apparatus
24 power source device
28 spindle unit
30 balance weight
60 sample fitting portion
61 sample board
61a pinhole
64 sample holder
66a to 69a ball plunger
66b to 69b adjusting screw
66a observation region
A observable centrifugal apparatus

BEST MODE FOR CARRYING OUT THE INVENTION

First Embodiment

An observable centrifugal apparatus according to a first embodiment will hereinafter be described with reference to the accompanying drawings. FIGS. 1 through 5 illustrate an observable centrifugal apparatus (which will hereinafter be also simply termed a [device]) A according to the first embodiment, and the device A includes a rotary disc 4 which rotates about a predetermined rotary shaft 2, a reactor 6 which is disposed on the rotary disc 4, accommodates a sample and rotates together with the rotary disc 4, and a microscope 8 for visually observing a state of the sample within the reactor 6. The device A applies a centrifugal force to the sample within the reactor 6, thereby separating predetermined substances (a liquid, a solid body, a gas, or a mixture thereof) from the sample or synthesizing these substances.

Note that a size and a configuration of the device A, which are specifically a size and a configuration of the rotary disc 4, may be set corresponding to characteristics and the number of the samples that are centrifugally separated or synthesized, however, the first embodiment provides a case in which the rotary disc 4 is constructed as a disc having a diameter of 220 mm by way of one presumed example. Further, the reactor 6 accommodates the predetermined sample in its interior and is not, if enabling the sample to react to the centrifugal separation or centrifugal synthesization, particularly limited in its mode, and, though the reactor 6 taking an optional mode can be selected and applied, a case of applying a chip-type reactor 6 is presumed by way of one example in the first embodiment. The reactor 6 is fixed to the rotary disc 4 in such a state that the reactor 6 accommodates the sample in its internal portion, and rotates together with the rotary disc 4.

In this type of device A, the microscope 8 is fixed to a predetermined position on the rotary disc 4 so as to enable a state of the sample within the reactor 6 to be observed. The rotary disc 4 is fitted with an imaging device 10 for photographing a microscope image of the sample state within the reactor, which is caught through the microscope 8, and with an image wireless transmission device 12 for wirelessly transmitting the microscope image photographed by the imaging device 10 as a dynamic image in real time. The microscope 8 in the first embodiment is constructed by including, by way of one example, an objective lens 8a which catches the state of the sample within the reactor 6, and a lens barrel 8b formed inside with a light path for transmitting the microscope image caught by the objective lens 8a to the imaging device 10. Moreover, a variety of imaging devices capable of imaging the state of the sample within the reactor 6 as the microscope image caught by the microscope 8 can be applied to the imaging device 10, however, the first embodiment provides a case where a CCD camera is applied to the imaging device 10 by way of one presumed example.

In this case, in the microscope 8, the light path of the microscope 8 is partially refracted at a predetermined angle to a disc surface (an upper surface in FIG. 4) 4a of the rotary disc 4 within the lens barrel 8b, and the imaging device (which will hereinafter be referred to as a CCD camera) 10 is positioned in the vicinity of the center of rotation of the rotary disc 4 so as to enable the microscope image described above to be caught on the light path of the microscope 8, which is refracted by the predetermined angle. Note that in the following discussion, the light path of the microscope 8 described above is called an observation light path, and the light traveling along the observation light path is called observation light.

In the first embodiment, by way of one example, a mirror 14 is disposed within the lens barrel 8b of the microscope 8 so that the mirror 14 is inclined at a predetermined angle to the observation light path, which is set optionally corresponding to a refraction angle of the observation light path. In the configuration illustrated in FIG. 4, the device A takes a structure that the objective lens 8a of the microscope 8 catches the state of the sample within the reactor 6 from upward in vertical directions (in the up-and-down directions in FIG. 4), and that the CCD camera 10 photographs the microscope image caught by the objective lens 8a in a direction parallel (horizontal) to the disc surface 4a of the rotary disc 4 in the vicinity of the center of rotation of the rotary disc 4. Therefore, the mirror 14 is disposed within the lens barrel 8b of the microscope 8 in a way that tilts the mirror 14 backward at an angle of approximately 135° to an entering direction of observation light n in FIG. 4, whereby the entered observation light n is refracted at approximately 90° and made to further travel so as to become parallel to the disc surface 4a of the rotary disc 4. The microscope 8 may take the configuration of forming the observation light path refracted substantially at a right angle within the lens barrel 8b by refracting the lens barrel 8b substantially at the right angle.

In this case, an available configuration is that the traveling direction of the observation light n is changed by positioning the microscope 8 at a peripheral edge of the rotary disc 4 so that the observation light n entering from the vertical direction is refracted in parallel with the disc surface 4a of the rotary disc 4 by the mirror 14 toward the central direction from the peripheral direction of the rotary disc 4. As a result, the microscope 8 takes a structure that the observation light n (i.e., the microscope image) reaches (converges) toward the center of rotation of the rotary disc 4, and it is feasible to have a configuration enabling the CCD camera 10 to catch the observation light n of the microscope in the vicinity of the center of rotation of the rotary disc 4, to be specific, enabling the camera 10 to photograph the microscope image.

Therefore, the CCD camera 10 can be positioned in the vicinity of the center of rotation of the rotary disc 4, and, even when the centrifugal force is generated by rotating the rotary disc 4, it is possible to reduce the centrifugal force acting on the CCD camera 10 and to photograph the microscope image with the CCD camera 10 stably at all times without any hindrance against the performance of the CCD camera 10 and any blurring of the microscope image when photographed due to the centrifugal force.

Further, as described above, the microscope 8 takes the structure in which the observation light path is refracted by the mirror 14, whereby a height (which is a distance in the up-and-down directions in FIG. 4) of the lens barrel 8b of the microscope 8 can be restrained. With this contrivance, even if rotating vibrations are generated by rotating the rotary disc 4, rigidity of the microscope 8 against the rotating vibrations can be increased, and the state of the sample within the reactor 6 can be observed invariably stably via the microscope 8. It is, however, preferable for restraining the height of the lens barrel 8b to structure the microscope 8 so that the refraction angle of the observation light path is larger than 0° but equal to or smaller than 90°.

The microscope 8 has the structure in which the lens barrel 8b thereof is movable up and down in the vertical directions (in the perpendicular directions (the up-and-down directions in FIG. 4)) with respect to the reactor 6, and, this structure enables a distance (a focal length) between the reactor 6 (specifically the sample) and the objective lens 8a to be adjusted. In this case, the structure is that the rotary disc 4 is provided with a guide (which will hereinafter be termed a Z-axis guide) 20 extending to a predetermined length in the vertical direction with respect to the disc surface 4a thereof, and the lens barrel 8b is slid along the Z-axis guide 20, whereby the microscope 8 adjusts the focal length between the sample and the objective lens 8a.

Further, in the first embodiment, the objective lens 8a of the microscope 8 and the reactor 6 are housed in an interior of the same component (which will hereinafter be referred to as a fixation component) 16, and the housed objective lens 8a and reactor 6 are fixed integrally with the fixation component 16 onto the rotary disc 4, thereby minimizing relative displacement between the objective lens 8a and the reactor 6 due to external vibrations (specifically, the rotating vibrations caused by the rotation of the rotary disc 4). With this contrivance, the microscope 8 can catch the state of the sample within the reactor 6 as the clear image without any blurring with the stability at all times, and it is feasible to precisely and surely observe the state of the sample in the process of the separation or the synthesization.

Figure 2:
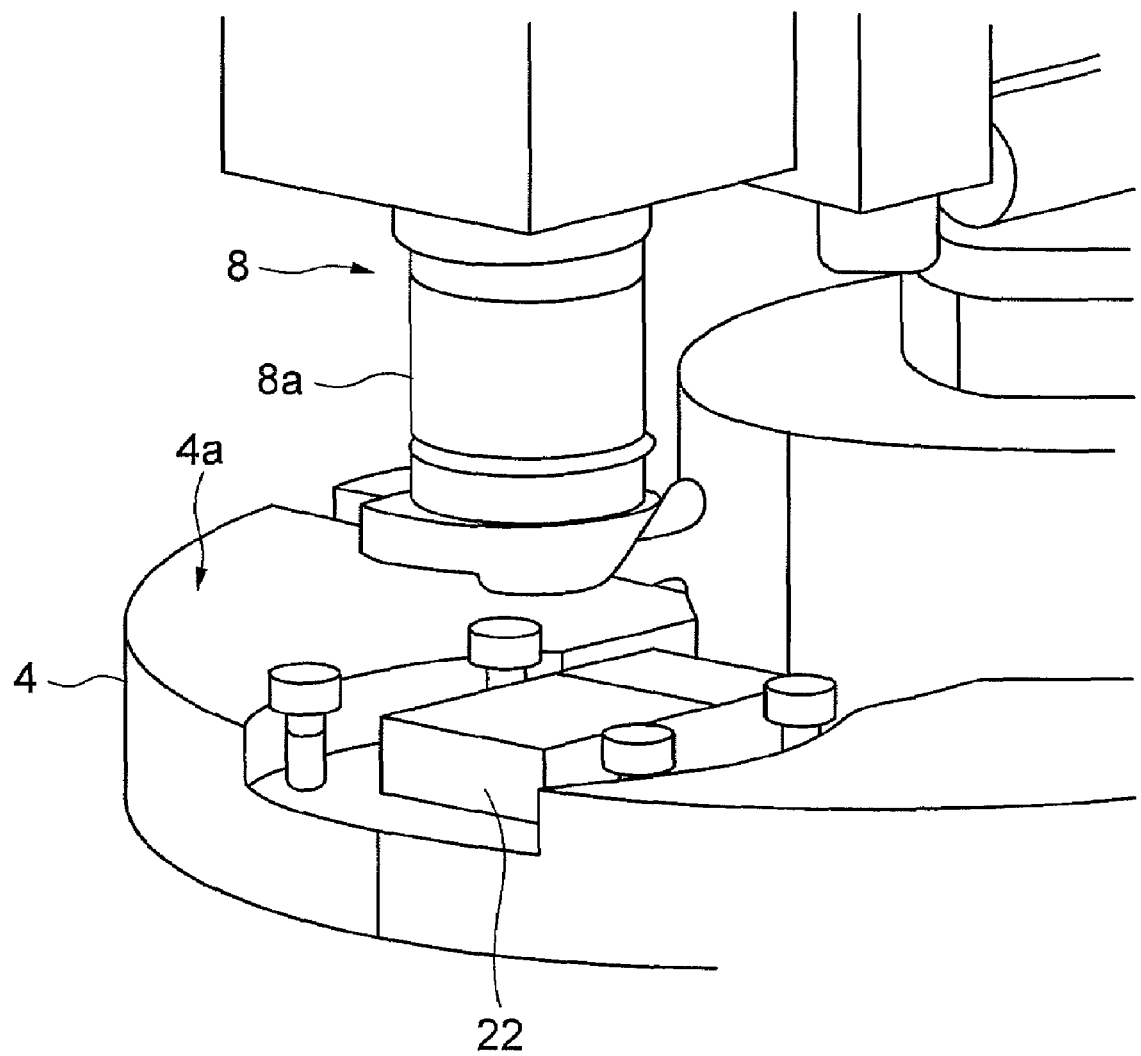
[FIG. 2] A view of a partial configuration, illustrating an internal configuration of a fixation component in FIG. 1.

In this case, the interior of the fixation component 16 is, as depicted in FIG. 2, provided with a predetermined illumination apparatus (e.g., an edge-type LED (Light Emitting Diode) LED backlight) 22, and the sample is illuminated with the light of the illumination apparatus 22 from the opposite side to the objective lens 8a of the microscope 8 and can be thus observed in a light-transmitted state. With this contrivance, the state of the sample within the reactor 6 can be observed more clearly, and the objective lens 8a can catch the state of the sample as the clearer microscope image. Incidentally, an LED 22a defined as a light source of the illumination apparatus (edge-type LED backlight) 22 is, in the same way as the CCD camera 10 described above is, positioned in the vicinity of the center of rotation of the rotary disc 4 in order to reduce the action of the centrifugal force generated by rotating the rotary disc 4.

Herein, the illumination apparatus 22 is, if the sample is illuminated with the light and can be observed in the light-transmitted state, not particularly limited in terms of the specific configuration thereof. For example, an optional illumination apparatus may be selected corresponding to the characteristics and the type of the sample, and an LED illumination (edge-type LED backlight) MEBL-CW25 made by Moritex Corp. is given by way of one example of the illumination apparatus in the first embodiment. For instance, however, an illumination apparatus having the performance equal to or higher than the illumination apparatus 22 described above may also be available.

Moreover, the fixation component 16 fixes a relative position between the objective lens 8a and the sample, to be specific, a height of the objective lens 8a with respect to the sample in a state where the proper distance is set by adjusting the focal length between the objective lens 8a of the microscope 8 and the sample. With this contrivance, it is feasible to keep, at a fixed level, the height of the objective lens 8a of the microscope 8 with respect to the sample and to observe the state of the sample with the stability during the separating reaction or the synthesizing reaction.

Further, in the first embodiment, the rotary disc 4 is fitted with the image wireless transmission device 12 for wirelessly transmitting the caught-by-camera image (photographed image) of the microscope image photographed by the CCD camera 10 as the dynamic image in real time together with the CCD camera 10 which photographs the microscope image described above as the dynamic image.

Thus, the system for transmitting the image photographed by the CCD camera 10 to an external receiver (unillustrated) involves adopting not a wired system but the wireless system, whereby there is neither a necessity for taking signal lines out of these devices nor a necessity for taking an extension layout of the signal lines into consideration even when the CCD camera 10 and the image wireless transmission device 12 are rotated together with the rotary disc 4. As a result, the peripheral structures of the CCD camera 10 and the image wireless transmission device 12 can be easily simplified.

Furthermore, because of no necessity for taking the extension layout of the signal lines into consideration, it is feasible to adopt the structure that the CCD camera 10 and the image wireless transmission device 12 are rotated together with the rotary disc 4 (specifically, the microscope 8 and the sample within the reactor 6), the CCD camera 10 can photograph the microscope image at an optional frame rate (frame count) without being restrained by the number of rotation of the rotary disc 4, and the caught-by-camera image of the photographed microscope image can be transmitted to the external receiving device (unillustrated).

This being the case, a display unit such as a liquid crystal panel and a CRT (Cathode Ray Tube) display are provided as the external receiving device, and the separating reaction or the synthesizing reaction of the sample can proceed while checking the caught-by-camera image (i.e., the state of the sample within the reactor 6) described above on the display unit in real time. Further, a behavior of the sample (specifically, the internal substance, the separating substance or the synthesizing substance thereof) is monitored by analyzing the caught-by-camera images recorded through a personal computer, an optimal rotating condition (which is, if comprehended in another aspect, an optimal magnitude of the centrifugal force acting on the sample) of the rotary disc 4 is estimated, and the rotation of the rotary disc 4 can be controlled under the estimated optimal condition (e.g., a rotating velocity and rotating time).

In this case, the image wireless transmission device 12 is, in the same way as the CCD camera 10 described above is, positioned in the vicinity of the center of rotation of the rotary disc 4 in order to reduce the action of the centrifugal force generated by rotating the rotary disc 4, and wirelessly transmits image data of the caught-by-camera image photographed by the CCD camera 10 to the external receiving device (the display unit such as the liquid crystal panel and the CRT display, which is connected to the receiver) from a predetermined antenna 18. Further, the antenna 18 is erected similarly in the vicinity of the center of rotation of the rotary disc 4, to be specific, erected on an extension line of the center of rotation of the rotary disc 4 in order to reduce the action of the centrifugal force generated by rotating the rotary disc 4.

When the image wireless transmission device 12 wirelessly transmits the image data (image signals) of the caught-by-camera image to the external receiving device (unillustrated), a transmission velocity (bit rate) of the image data and a data format (a frequency, compressed-data or non-compressed data, etc) may optionally be set corresponding to the using mode and the using conditions of the device A. One example in the first embodiment is that the image wireless transmission device 12 converts the caught-by-camera image of the microscope image photographed by the CCD camera 10 into the image data of non-compressed digital signals having a frequency of 2.4 GHz, and wirelessly transmits the thus-converted image data to the external receiving device. The image signals transmitted from the image wireless transmission device can be further transmitted to the external receiving device without any loss of the image signals, and the separating reaction or the synthesizing reaction can proceed while checking the state of the sample in the clear and stable image in the external receiving device. The image data transmitted to the external receiving device from the image wireless transmission device 12 may be the compressed signals and may also be analog signals in place of the non-compressed digital signals described above.

Herein, the CCD camera 10, if capable of photographing the microscope image of the state of the sample within the reactor 6 that is caught by the microscope 8, is not particularly limited to the specific configuration thereof. For example, an optional CCD camera may be selected corresponding to the using mode and the using conditions of the device A, and, to give one example, in the first embodiment, a color board camera MSC-90 made by Moswell Co., Ltd. is employed. The CCD camera having the performance equal to or higher than the CCD camera 10 may, however, be available.

Moreover, the image wireless transmission device 12, if capable of wirelessly transmitting the caught-by-camera image of the microscope image photographed by the CCD camera 10 to the external receiving device (unillustrated), is not particularly limited in terms of the specific configuration thereof. For example, an optional image wireless transmission device may be selected corresponding to the using mode and the using conditions of the device A, and the first embodiment involves using TRX24mini made by I-Den Videotronics Co., Ltd. by way of one example. For instance, the image wireless transmission device having the performance equal to or higher than the image wireless transmission device 12 may, however, be available.

Figure 3:
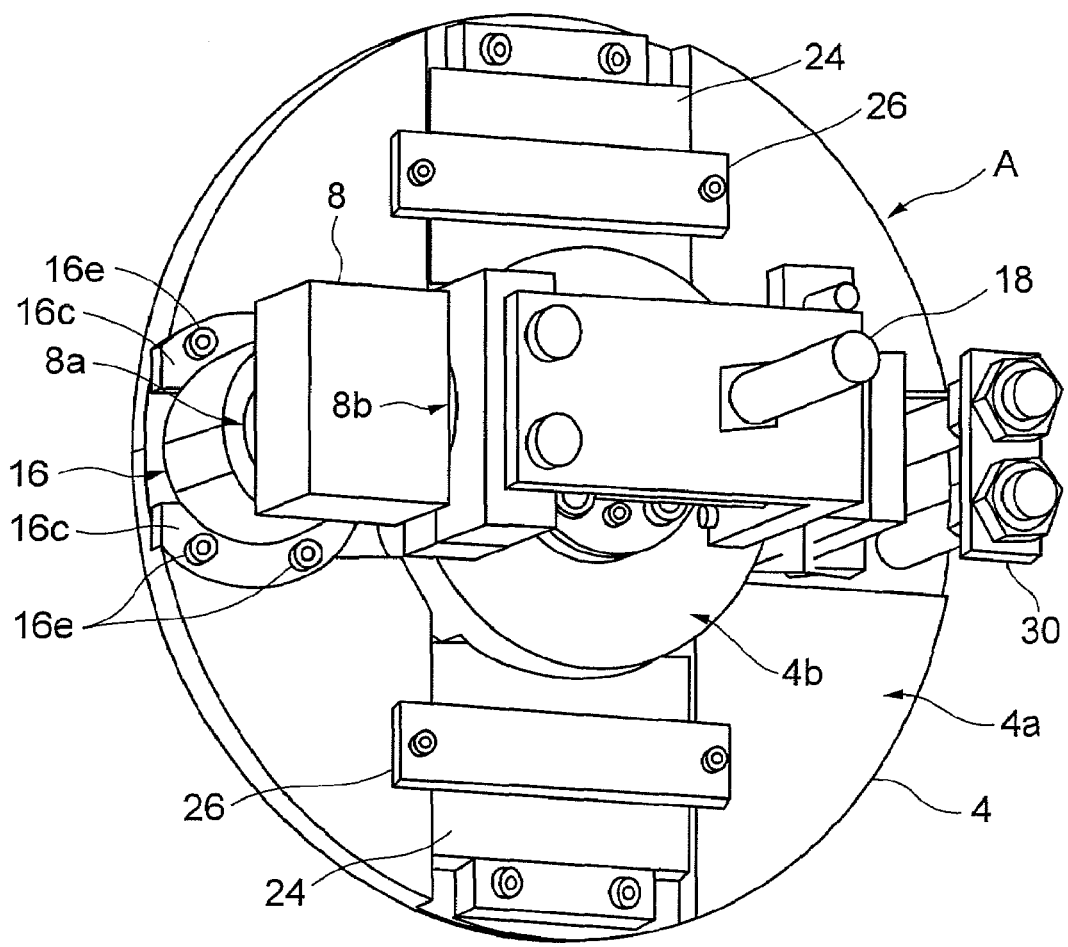
[FIG. 3] A top view of the example of the whole configuration of the observable centrifugal apparatus in FIG. 1 as viewed from upward.

The variety of electric and electronic components such as the CCD camera 10, the image wireless transmission device 12 and the illumination apparatus 22 provided in the device A are, as illustrated in FIGS. 1 and 3, driven by a predetermined power source device (e.g., a battery) 24. In this case, the power source device 24, if capable of stably supplying the power enabling the variety of electric and electronic components (the CCD camera 10, the image wireless transmission device 12 and the illumination apparatus 22) to normally operate during the separating reaction or the synthesizing reaction to the sample, is not particularly limited in terms of its specific configuration. For instance, an optional power source device may be selected corresponding to the magnitude of the power required by the variety of electric and electronic components, and the first embodiment involves using a battery UBBP01 (which is 3.7 V in voltage and 1.8 Ah in battery capacity) made by ULTRA LIFE Co., Ltd. by way of one example. For instance, the power source device having the performance equal to or higher than the image power source device 24 may, however, be available.

In the first embodiment, four pieces of power source devices (batteries) 24 are employed in series, and these four batteries 24 are disposed equally by twos in positions symmetric with respect to the center of rotation of the rotary disc 4 (with a phase difference of 180°) as well as being disposed with a phase difference of 90° with respect to the microscope 8, the reactor 6 and the fixation component 16 (refer to FIG. 3). In this case, to give one example, the battery 24 is embedded in a fitting portion formed by concaving the disc surface 4a of the rotary disc 4, then fixed by a plate-like member 26 and thus fitted to the rotary disc 4.

Figure 4:
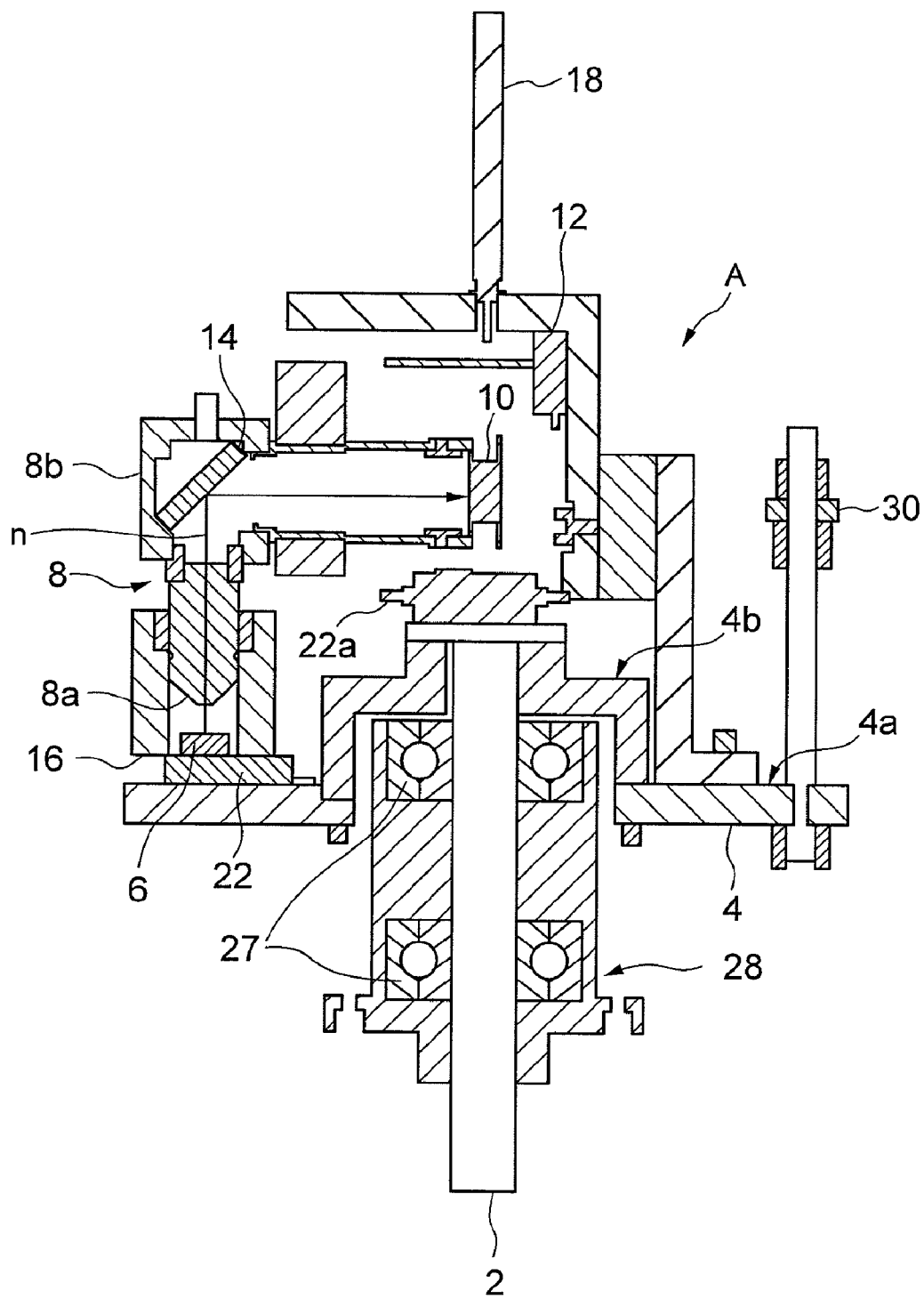
[FIG. 4] A vertical sectional view of the observable centrifugal apparatus in a state where a spindle unit is fitted to a rotary disc in FIG. 1.
Figure 5:
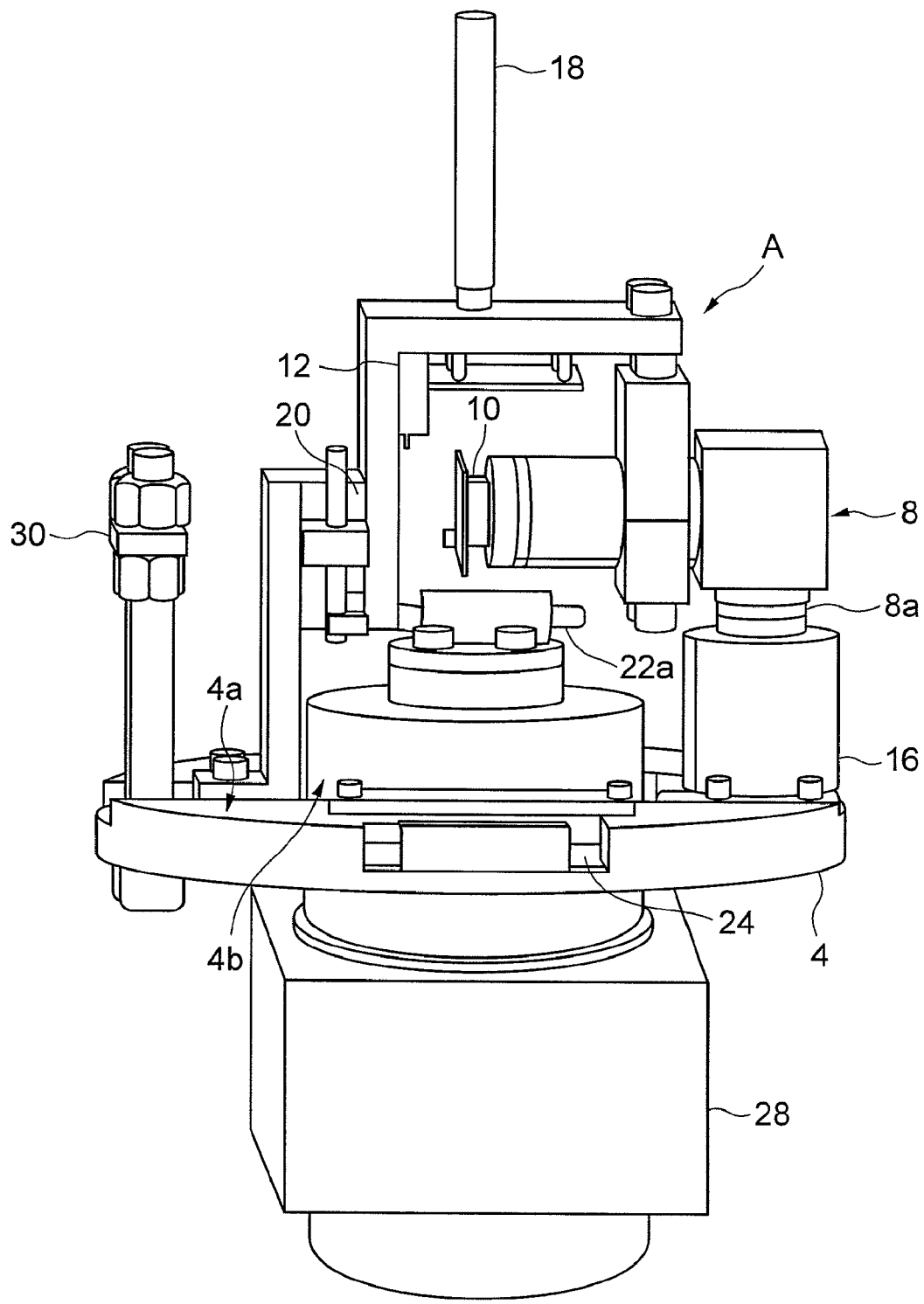
[FIG. 5] A perspective view of the whole observable centrifugal apparatus in a state where an air spindle unit 28 is fitted as the spindle unit.

Herein, in the device A, the rotary shaft 2 of the rotary disc 4 is rotated by an unillustrated predetermined driving device (e.g., a spindle motor, etc) and is ratably supported by a variety of bearings 27, in which FIG. 4 illustrates as one example a configuration that the rotary shaft 2 is supported by such a rolling bearing that balls are applied as rolling members. In this case, the rolling bearing 27 may also be a bearing in which a variety of rollers (a cylindrical roller, a tapered roller, a spherical roller, etc) in addition to the variety of ball bearings in which the balls are applied as the rolling members. Further, the configuration depicted in FIG. 4 takes the structure of supporting the rotary shaft 2 with the two bearings 27, however, the rotary shaft 2 may also be supported by the single bearing 27 and may further be supported by three or more bearings 27.

Incidentally, an air bearing substituting for the variety of rolling bearings described above is applied as the bearing 27, and the rotary shaft 2 is rotatably supported by the air bearing, thereby enabling the rotating vibrations caused when rotating the rotary disc 4 to be reduced remarkably, restraining by extension the rotating vibrations of the microscope 8 and the CCD camera 10, and enabling the state of the sample to be observed and photographed during the separating reaction or the synthesizing reaction, which is further preferable. Herein, to exemplify one example, the air bearing takes a structure that a cylindrical housing positioned to cover an external peripheral surface of the rotary shaft 2 along its entire periphery rotatably supports the rotary shaft 2, the air is blown out toward the outer peripheral surface of the rotary shaft 2 via a plurality of blast nozzles (blast holes) formed in an inner peripheral surface (opposite to the outer peripheral surface of the rotary shaft 2) of the housing, and the inner peripheral surface of the housing and the outer peripheral surface of the rotary shaft 2 are kept in a non-contact state, whereby the rotary shaft 2 is rotated extremely smoothly.

Further, in the first embodiment, the structure is that the rotary shaft 2 and the bearing 27 rotatably supporting the rotary shaft 2 are constructed integrally with the housing into a spindle unit 28, and the spindle unit 28 is fitted to the rotary disc 4, whereby the rotary disc 4 is rotated about the rotary shaft 2. In this case, the rotary disc 4 is provided with a spindle unit fitting portion 4b, of which a central portion is protruded upward (on the side of disposing the microscope 8, the reactor 6, the CCD camera 10 and the image wireless transmission device 12) in a convex shape in a predetermined size, formed by hollowing in the convex shape the lower side (opposite to the side of disposing the respective components described above) of the rotary disc 4, and the spindle unit 28 is inserted in the spindle unit fitting portion 4b from the lower side of the rotary disc 4 and thus fitted to the rotary disc 4.

Thus, the device A takes the structure that the spindle unit 28 is covered with the rotary disc 4, whereby it is feasible to reduce a distance between the center of rotational gravity when rotating the rotary disc 4 on which to dispose the microscope 8, the reactor 6, the CCD camera 10 and the image wireless transmission device 12 and the shaft supporting portion at which the rotary shaft 2 is rotatably supported by the bearings 27 and to effectively decrease rotation moment caused at the shaft supporting portion.

The first embodiment described above did not discuss especially materials of the components of the device A, however, a variety of materials may be optionally selected and used corresponding to the using mode and the using conditions of the device A. One example in the first embodiment is that a high-strength aluminum alloy (A2017) is used as a material of the rotary disc 4 and of the variety of fitting members for fitting the microscope 8, the reactor 6, the CCD camera 10 and the image wireless transmission device 12 to the rotary disc 4, thereby scheming to reduce the weights of these members while ensuring sufficient rigidity when rotated.

Moreover, in the first embodiment, a deflection stress on the spindle unit 28, which is caused when rotated, is decreased by equalizing a weight balance of the device A when rotated, and hence a predetermined balance weight 30 for the rotary disc 4 is provided in a position (on the opposite side with respect to the center of rotation) that is substantially symmetric to the positions of disposing the microscope 8 and the reactor 6 with respect to the center of rotation. It may be sufficient that a weight and a disposing position of the balance weight 30 are adjusted so as to reduce the defection stress on the spindle unit 28 described above in accordance with the weights of the variety of members such as the microscope 8, the reactor 6, the CCD camera 10 and the image wireless transmission device 12 that are disposed on the rotary disc 4 and the balance (the center of gravity) thereof.

Incidentally, the device A, in the case of observing the separating reaction or the synthesizing reaction to the sample with higher accuracy, may have a configuration that an air spindle unit with the rotary shaft 2 rotatably supported by the air bearing described above is attached as the spindle unit 28 to the rotary disc 4. With this configuration, the rotating vibrations generated when the rotary disc 4 rotates can be remarkably reduced, and the state of the sample during the separating reaction or the synthesizing reaction can be observed through the caught-by-camera image with the stable and high image quality. In this case, the air spindle unit can involve using, e.g., GBS100H made by NSK Ltd. and so on.

Given next is an explanation about an operational effect acquired by attaching, as described above, the reactor 6 to the observable centrifugal apparatus A, getting the centrifugal force generated by rotating the reactor 6 to act on the fluid, and thus driving and flowing the fluid.

The reactor 6 has neither the fluid-connection to the external device (if the fluid driving involves making use of a pump) nor the electric connection to the external device (if the fluid driving involves making use of, e.g., an electroosmotic flow), whereby the structure can be simplified. An effect thereof is that the reactor 6 becomes easy to handle, the automation is facilitated, and an analyzing velocity is improved. Further, the reactor 6 can be further downsized, with the result that a minuter sample can be analyzed. In this case, cells can not be electrically broken and can therefore be broken by mechanical collisions. Moreover, the peripheral devices can be also downsized, thereby enabling the whole measuring system to be downsized Further, the fluid can be driven without being affected by chemical characteristics of the sample. Especially, even a sample composed mainly of a solution, which is easy to be electrically resolved by applying an electric field, can be driven (analyzed). Moreover, it is preferable that the applied range expands to a sample having a possibility of altering due to an electrical stimulus because of being utilized without being aware of the influence thereof.

Furthermore, the centrifugal separation effect of the sample can be simultaneously generated, and the sample can be separated with a specific gravity.

Moreover, it is possible to grasp the detection state without any loss of the information (the loss of frames) even with the reaction in a region showing a low number of rotation (low centrifugal force) by making use of the observable centrifugal apparatus according to the first embodiment.

Second Embodiment

Figure 6:
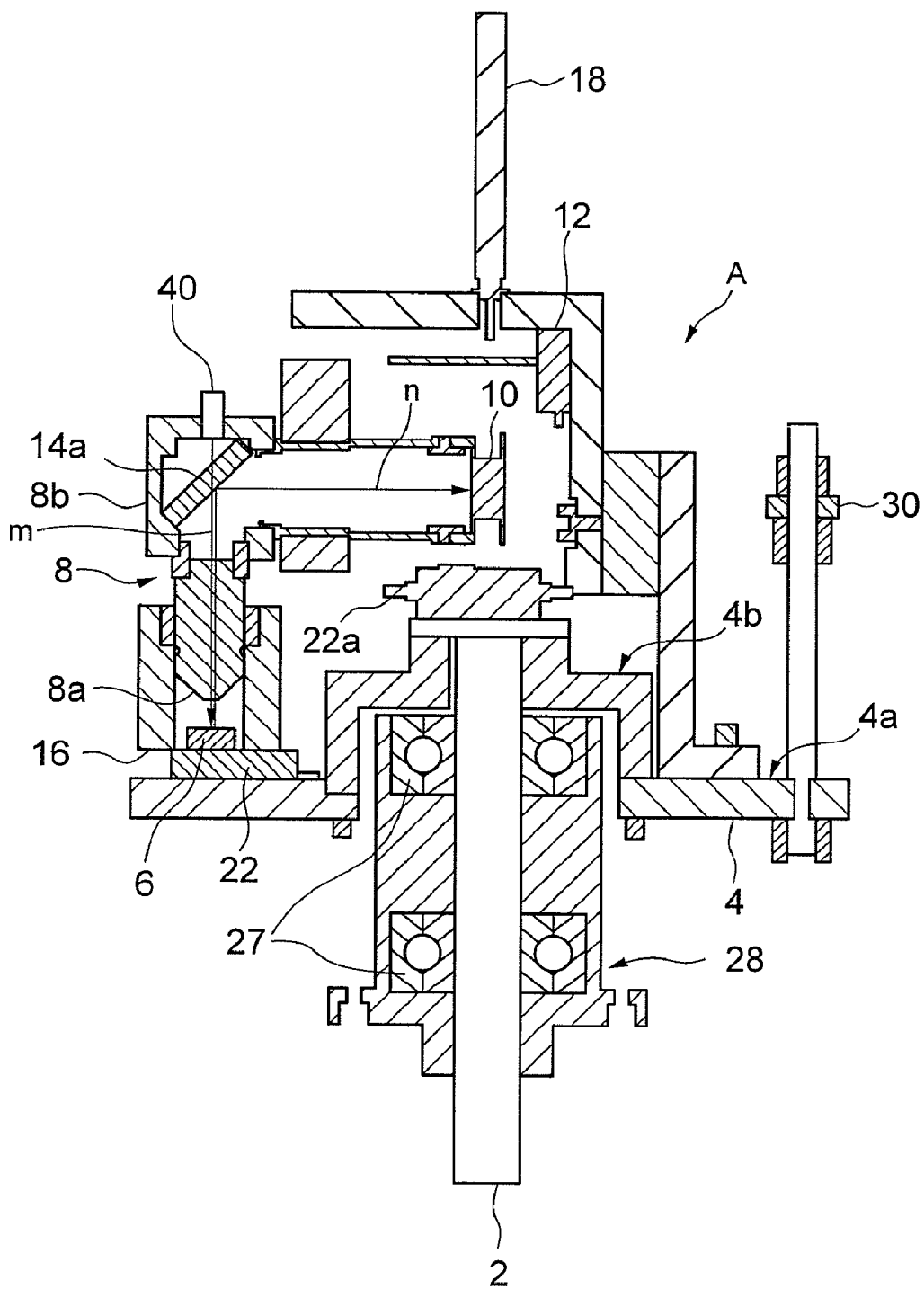
[FIG. 6] A vertical sectional view, similar to FIG. 4, illustrating a configuration according to a second embodiment in which an epi-illumination apparatus is added to the observable centrifugal apparatus A.

Next, a configuration of a second embodiment where an epi-illumination apparatus for illuminating the sample with the light from upward is added to the observable centrifugal apparatus A in FIGS. 1 through 5, will be described with reference to FIG. 6. FIG. 6 is a vertical sectional view, similar to FIG. 4, illustrating the configuration of the second embodiment in which the epi-illumination apparatus is added to the observable centrifugal apparatus A.

In the case of observing the substance having substantially the same optical transmittance (transparency) as the background such as the cell in the solution and glass beads, under the illumination by the backlight from the illumination apparatus 22, it is difficult to obtain light and shade (contrast) depending on a shape, with the result that the observation is difficult to attain. A measure to cope with this difficulty involves, as depicted in FIG. 6, providing the observable centrifugal apparatus A with the epi-illumination apparatus in the second embodiment.

To be specific, the mirror above the objective lens 8a is constructed as a half mirror 14a, and an LED illumination unit 40 is provided above the half mirror 14a, thus configuring a coaxial illumination (epi-illumination) apparatus. Illumination beams m emitted from the LED illumination unit 40 penetrate the half mirror 14a and irradiate over the sample within the reactor 6 via the objective lens 8a. Further, reflected beams (observation beams) n from the sample are reflected by the half mirror 14a via the objective lens 8a and reach the CCD camera 10. The illumination apparatus 22 may be omitted in FIG. 6.

The LED illumination unit 40 can involve utilizing a high-luminance green LED (100047 Series showing Φ3 mm and 6800 mcd in light intensity, made by OPTSOURCE Ltd.) available on the market, however, a color tone and the luminance can be selected depending on the object sample. Further, if concerned about a damage to the LED by the centrifugal strength (the number of rotation, the time), the light can be led via an optical fibre to the microscope by disposing the light source (LED) in the vicinity of the center of the rotation.

According to the configuration with the addition of the epi-illumination apparatus in FIG. 6, the light and shade (contrast) due to the reflection on the surface of the sample can be acquired, even when the optical transmittance of the sample is substantially the same as the background, by observing the reflected beams from the sample within the reactor 6, and hence the behavior of the sample can be clearly observed.

Figure 10:
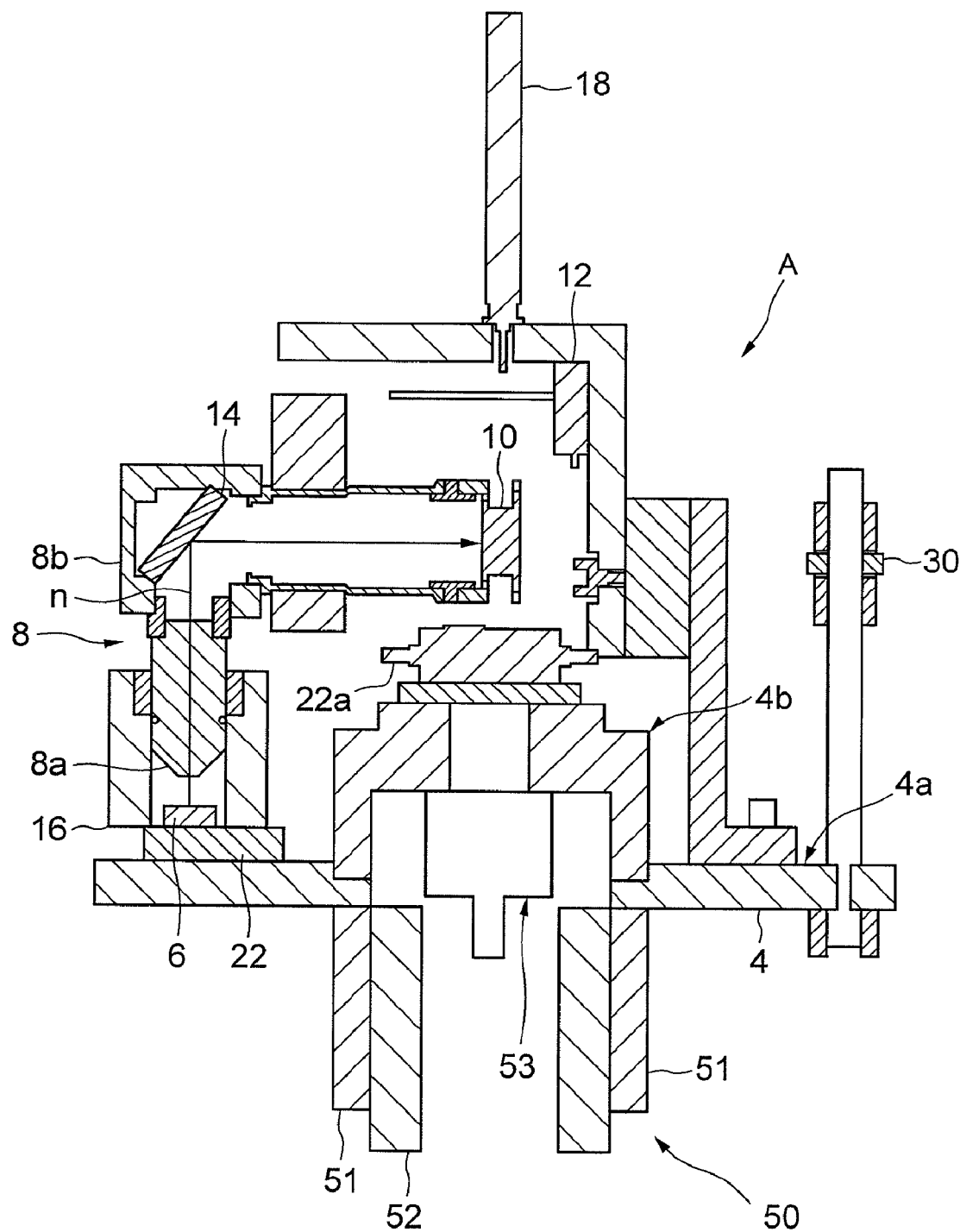
[FIG. 10] A vertical sectional view, similar to FIG. 4, depicting a modified example in which a rotary disc 4 of the observable centrifugal apparatus A is driven by a direct drive motor.

The observable centrifugal apparatus A described above is requested to have the observability especially in a low-velocity region in order to generate the comparatively low centrifugal force (excessive gravity that is approximately several times as large as the gravity) for the purpose of measuring a geotactic behavior of a minute organism, however, the observable centrifugal apparatus A in the first and second embodiments includes the microscope system mounted on the rotary disc, so that the dynamic image can be photographed at the high frame rate irrespective of the number of rotation, and the observable centrifugal apparatus A is optimal as a behavior observing apparatus particularly for the minute organism that is quick in motion. The same application requires the apparatus having a fast response to a change in the number of rotation in order to reproduce an abrupt change in the gravity environment. Such being the case, the observable centrifugal apparatus A may be configured so that the rotary disc 4 is, as depicted in FIG. 10, driven directly by a direct drive motor. To be specific, as illustrated in FIG. 10, a motor built-in type configuration is attained by fitting a rotary unit 51 positioned on the outer peripheral side of a direct drive motor 50 to the rotary disc 4. This configuration enables the responsibility to the change in the number of rotation to be improved and the downsized apparatus to be attained. For example, a PS motor (1006 Series) made by NSK Ltd. can be used as the direct drive motor 50.

Moreover, a slip ring 53 is fitted to a fitting portion 4b above the fixing unit 52 provided inwardly of the direct drive motor 50 in FIG. 10, whereby the image signals may be transmitted to the outside and the power may be supplied via the slip ring 53 if the image is invisible because of a long image sampling interval and in the case of requiring the consecutive observation of the object sample for a long period of time, which is remarkably slow in gravity reaction. Further, a centrifugal load test can be performed in a way that restrains the influence of the radio waves on the biomolecule sample in the case of the external device and the biometric application by employing the slip ring 53.

Third Embodiment

Next, a configuration of a third embodiment having further improved magnification and resolution for making observable a more minute object than the minute organism and the micro beads of polystyrene etc, will be described with reference to FIGS. 11A to 17C.

Figure 11A:
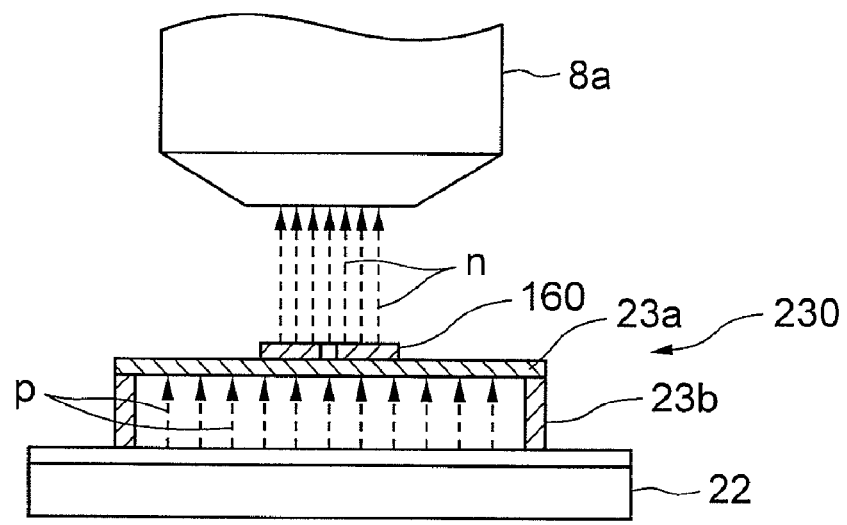
[FIG. 11A] A sectional view of the principal portion, depicting a conventional sample fitting portion.
Figure 11B:
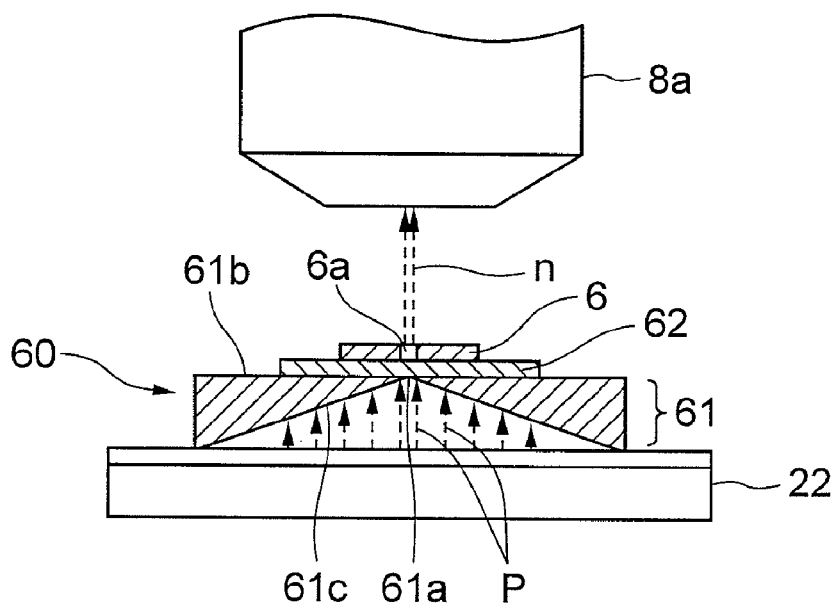
[FIG. 11B] A sectional view of the principal portion, depicting a sample fitting portion of the observable centrifugal apparatus A in a third embodiment.

FIG. 11A is a sectional view on the side of principal portions, showing an example of a conventional sample fitting portion, and FIG. 11B is a sectional view on the side of principal portions, showing an example of a sample fitting portion of the observable centrifugal apparatus A in the third embodiment.

As illustrated in FIG. 11A, for example, a sample board 230 has hitherto been provided between an observation object 160 and a backlight type illumination apparatus 22, and the sample board 230 includes a light translucent member 23a composed of a glass plate, a resin plate, etc, which is fitted in a way that places the observation object 160 thereon, and a board unit 23b erected from the surface of the illumination apparatus 22. Backlight illumination beams p emitted from the illumination apparatus 22 irradiate over the observation object 160 from the rear side via the translucent member 23a, and the transmitted beams serving as the observation beams n get incident on the objective lens 8a, whereby the sample within the observation object 160 can be observed.

By the way, in the case of disposing the sample board 230 as depicted in FIG. 11A on the observable centrifugal apparatus A described above, the centrifugal excessive gravity occurs on the sample board 230, and hence the sample needs designing in a small size with a light weight while particularly the optical system is required to be configured to the simplest possible degree. The Koehler illumination system and the critical illumination system, which are utilized for the general type of microscopes, have hitherto been known as measures for improving the resolution but need a condenser lens for converging the illumination beams, which is not proper for the application in the third embodiment. Such being the case, in the third embodiment, the sample fitting portion of the observable centrifugal apparatus A takes a structure as depicted in FIG. 11B in order to easily improve the resolution.

The sample fitting portion 60 illustrated in FIG. 11B includes a sample board 61 formed with a pinhole 61a substantially at the center and a cover member 62 composed of the glass plate, the resin plate, etc, which is disposed in a way that covers the pinhole 61a on a surface 61b of the sample board 61, and is provided between the reactor 6 defined as the observation object and the backlight type illumination apparatus 22. The reactor 6 is placed on and thus fitted to the cover member 62.

In contrast with the flat surface 61b, the undersurface of the sample board 61, on the side of the illumination apparatus 22, is formed in a cone-shape with the pinhole 61a being centered, i.e., the configuration is that an approximately conical-concave surface 61c inclined toward the pinhole 61a is formed, and an outer peripheral portion of the approximately conical-concave surface 61c is placed on the illumination apparatus 22. The sample board 61 can be composed of a light metal material such as aluminum and a resin material. The approximately conical-concave surface 61c in the interior of the sample board 61 undergoes, e.g., a black oxide treatment.

According to the sample fitting portion 60 in FIG. 11B, the sample board 61 formed with the pinhole 61a is installed on the illumination apparatus 22, whereby a part of the backlight illumination beams p emitted from the illumination apparatus 22 penetrate the pinhole 61a, the transmitted beams thereof irradiate over the observation region 6a of the observation object (the reactor 6) from the rear side, and the beams getting transmitted through the observation region 6a are incident as the observation beams n on the objective lens 8a, thereby enabling the sample within the reactor 6 to be observed. Thus, the transmitted beams penetrating the pinhole 61a irradiate over almost only the observation region 6a, so that the image contrast is improved, and the image with the high resolution is obtained.

The conventional backlight illumination as depicted in FIG. 11A takes the structure that the whole of the observation object is irradiated with the illumination beams p, and therefore the light (stray light) from other than the observation area (region) easily enters the objective lens 8a. If observed at a low magnification, these unnecessary beams affect small because of the broad observation region, however, in the case of observing the minute substance as in the application described above, the image resolution and the contrast are greatly affected. In comparison with this, the improvement is, as depicted in FIG. 11B, that the sample board 61 is formed with the pinhole 61a, and the transmitted beams, penetrating the pinhole 61a, of the backlight illumination beams p irradiate over only the observation region 6a, thereby enabling the improvements of the contrast and the resolution to be realized.

Further, the configuration that the approximately conical-concave surface 61c in the interior of the sample board 61 is formed in the cone-shape with the pinhole 61a being centered, enables the illumination beams emitted from the illumination apparatus 22 to be introduced to the pinhole 61a at the high efficiency and prevents the occurrence of the scattered light through the black oxide treatment over the approximately conical-concave surface 61c.

Next, a specific configuration of the sample fitting portion 60 in FIG. 11B will be described with reference to FIGS. 12 to 17C.

Figure 12:
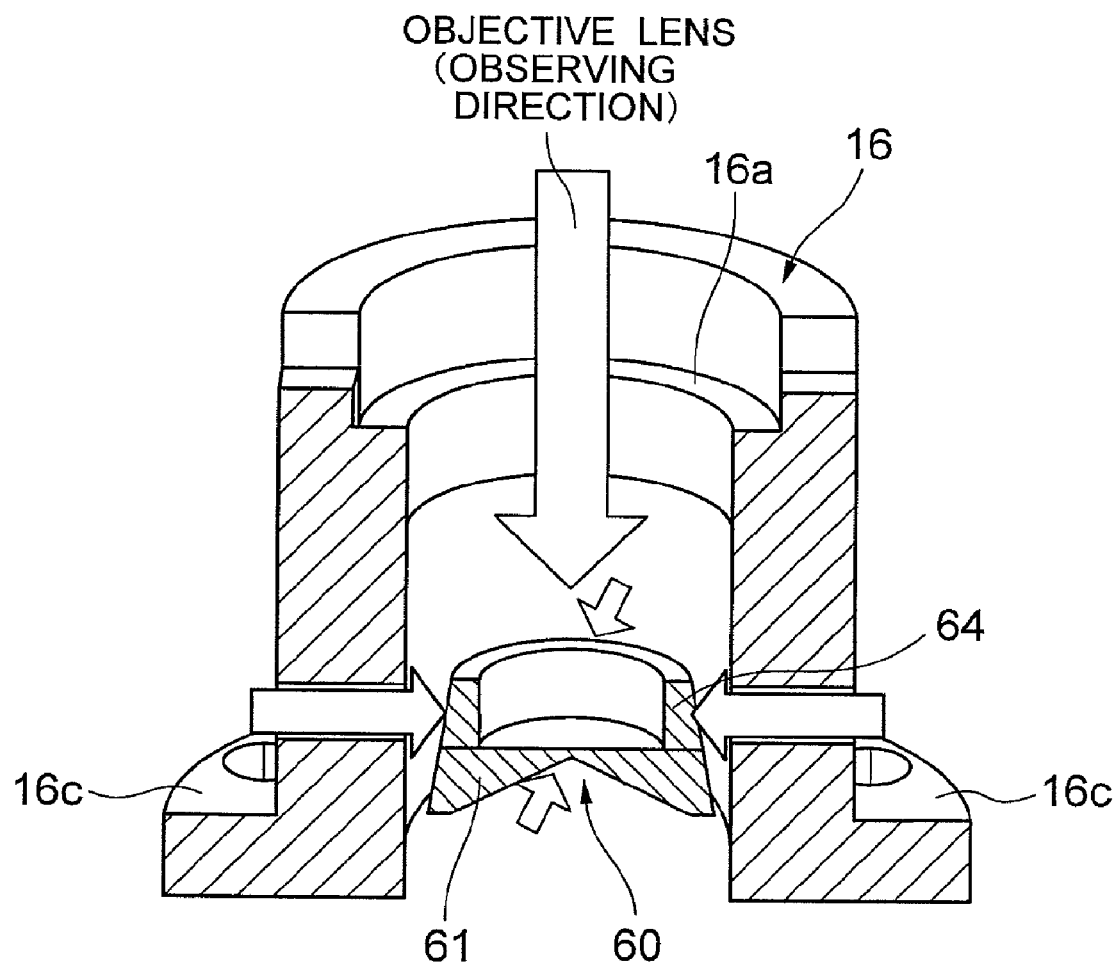
[FIG. 12] A fragmentary sectional perspective view illustrating a fixation component 16 of the observable centrifugal apparatus A and a sample fitting portion 60 provided in the interior of the fixation component 16 in FIG. 4.
Figure 13A:
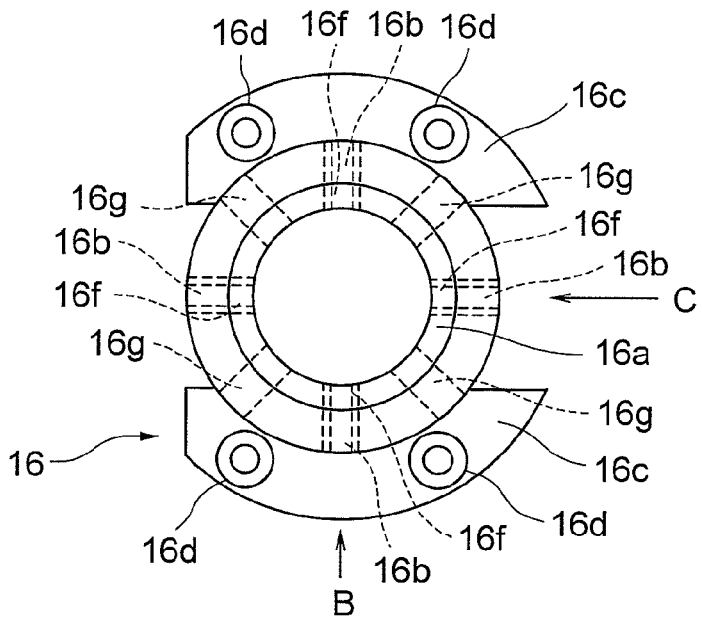
[FIG. 13A] A plan view of the fixation component in FIG. 12.
Figure 13B:
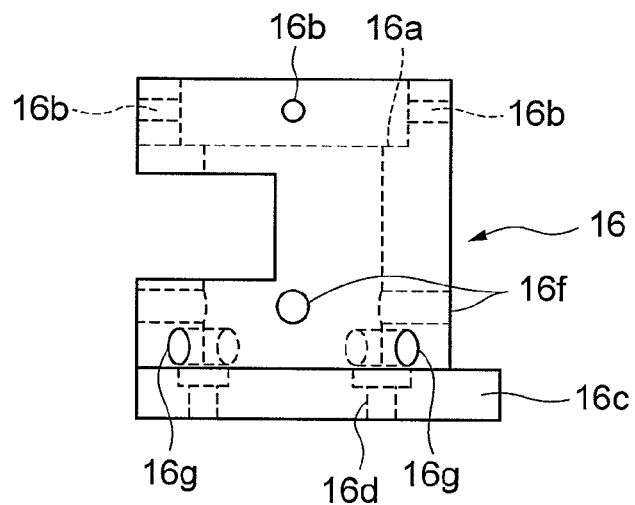
[FIG. 13B] A side view of the fixation component as viewed in a direction B in FIG. 13A.
Figure 13C:
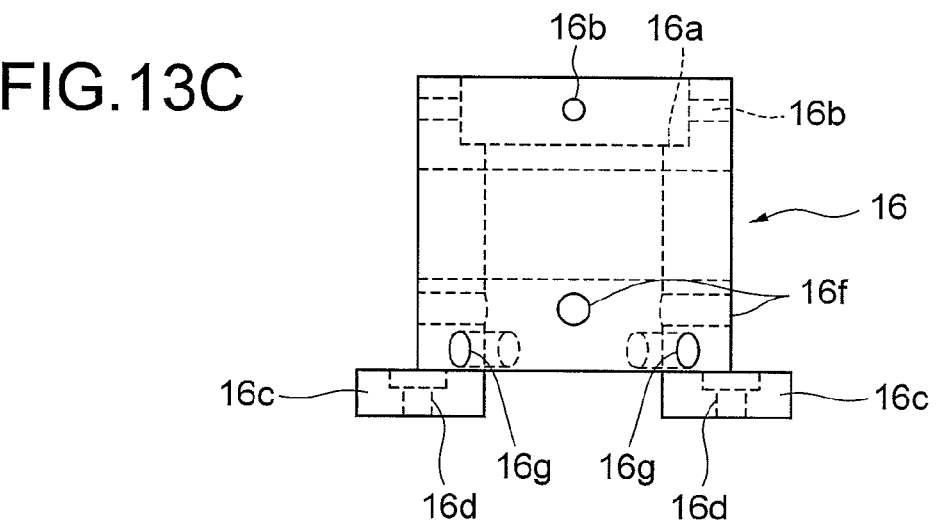
[FIG. 13C] A side view of the fixation component as viewed in a direction C in FIG. 13A.

FIG. 12 is a fragmentary sectional perspective view illustrating the fixation component 16 of the observable centrifugal apparatus A and the sample fitting portion 60 provided in the interior of the fixation component 16 in FIG. 4. FIG. 13A is a plan view of the fixation component in FIG. 12, FIG. 13B is a side view as viewed in a direction B, and FIG. 13C is a side view as viewed in a direction C.

As in FIG. 12 and FIGS. 13A to 13C, the fixation component 16 is constructed substantially in a cylindrical shape on the whole, the objective lens 8a in FIG. 4 is fitted to the objective lens fitting portion 16a of the upper part so that the observing direction of the objective lens 8a (FIG. 4) is coincident with the vertical direction indicated by an arrowhead in FIG. 12, and is fixed by screws (unillustrated) screwed into a plurality of screw holes 16b. Further, the fixation component 16 has a circular bottom 16c projecting on the outer peripheral side, and is fixedly secured to the rotary disc 4 with the screws 16e (FIG. 3) inserted into the plurality of screw holes 16d of the bottom 16c.

As depicted in FIG. 12, the sample fitting portion 60 is disposed at the bottom within the fixation component 16. The sample fitting portion 60 has the sample board 61 and a sample holder 64, which are positioned and held in biaxial directions respectively at four positions as indicated by arrowheads in the horizontal direction in FIG. 12. To be specific, as in FIGS. 13A to 13C, a plurality of screw holes 16f for positioning the sample holder 64 is provided in the outer peripheral surface of the lower part of the fixation component 16, and a plurality of screw holes 16g for positioning the sample board 61 is provided in the outer peripheral surface of a further lower part of the screw hole 16f.

Figure 14A:
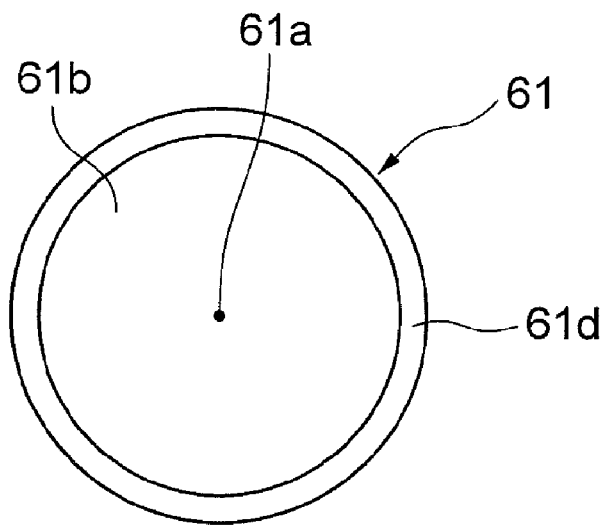
[FIG. 14A] A plan view of the sample board in FIG. 12.
Figure 14B:
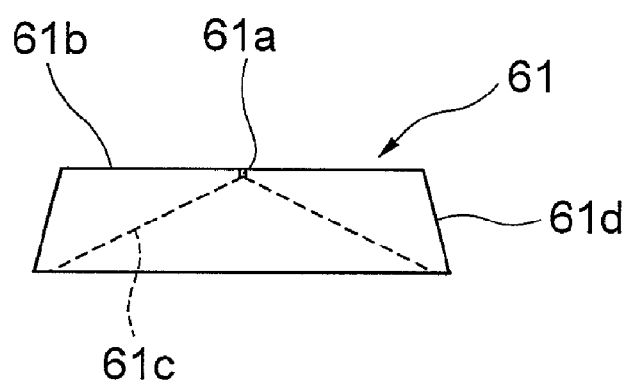
[FIG. 14B] A side view of the sample board in FIG. 12.
Figure 15A:
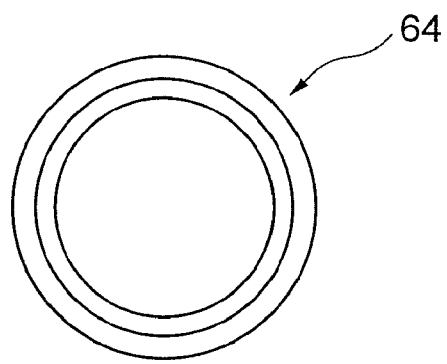
[FIG. 15A] A plan view of a sample holder in FIG. 12.

FIG. 14A is a plan view of the sample board in FIG. 12, and FIG. 14B is a side view. FIG. 15A is a plan view of the sample holder in FIG. 12, FIG. 15B is a side view, and FIG. 15C is a side view of the sample holder and the sample board in combination.

The sample board 61 in FIGS. 14A and 14B is configured in a truncated cone shape, the pinhole 61a is formed at the center of the surface 61b, and the approximately conical-concave surface 61c is formed on the side of the undersurface. An outer diametrical surface of the sample board 61 is an inclined surface 61d inclined to the bottom from the surface 61b.

The sample board 61 described above can be manufactured in a way that cuts off the interior of the conic member (which is, e.g., 21 mm in diameter of the upper portion, 24 mm in diameter of the lower portion and 6 mm in thickness) at an aperture angle 120° and forms a minute hole (pinhole) having a diameter of 0.400 mm in the upper surface. The sample board 61 is manufactured from, e.g., an A5052 aluminum alloy and is colored in black overall by a black anodic oxide coating treatment for preventing the scattered light.

Figure 15B:
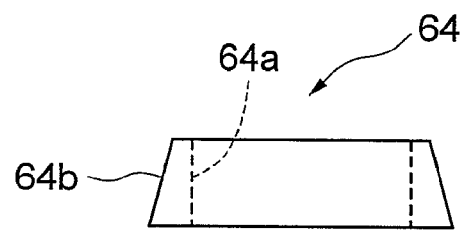
[FIG. 15B] A side view of the sample holder in FIG. 12.
Figure 15C:
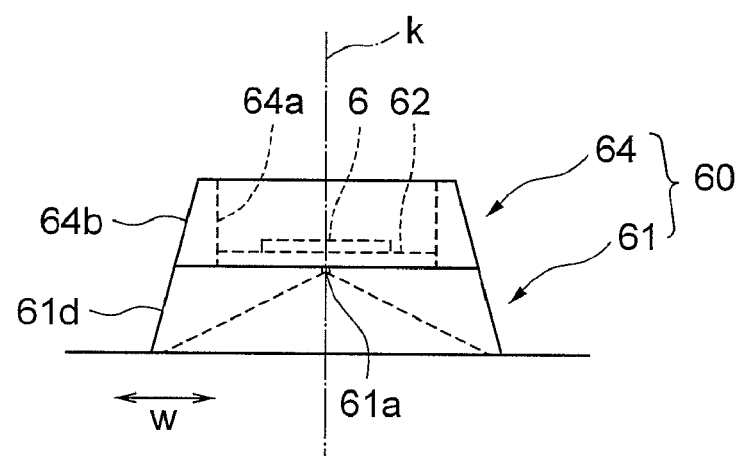
[FIG. 15C] A side view of a combination of the sample holder and the sample board in FIG. 12.

As in FIGS. 15A and 15B, the sample holder 64 is configured in the truncated cone shape, the interior thereof is formed with an inner peripheral portion 64a having a cylindrical surface, and its outer diametric surface is an inclined surface 64b inclined downward from upward in FIG. 15B. As in FIG. 15C, the sample holder 64 is disposed on a surface 61b of the sample board 61 and is slidable on the sample board 61 in a horizontal direction w. The cover member 62 is held by the inner peripheral portion 64a of the sample holder 64 on the surface 61b of the sample board 61.

The sample holder 64 as described above can be manufactured in such a configuration that the internal portion of the conic member (which is, e.g., 18 mm in diameter of the upper portion, 21 mm in diameter of the lower portion and 6 mm in thickness) is hollowed in the cylindrical shape having a diameter of 15 mm.

Figure 16A:
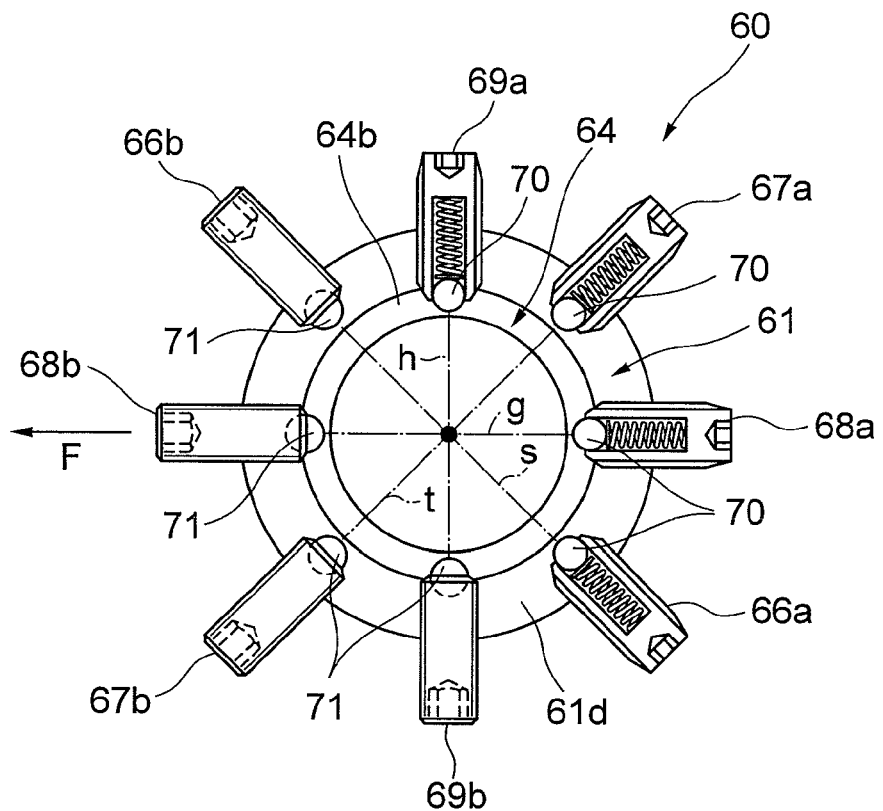
[FIG. 16A] A schematic diagram illustrating the sample board and the sample holder in FIG. 12 as viewed from upward (on the side of the objective lens) for explaining an alignment mechanism of the sample board and a position adjusting mechanism of the sample holder in FIG. 12.
Figure 16B:
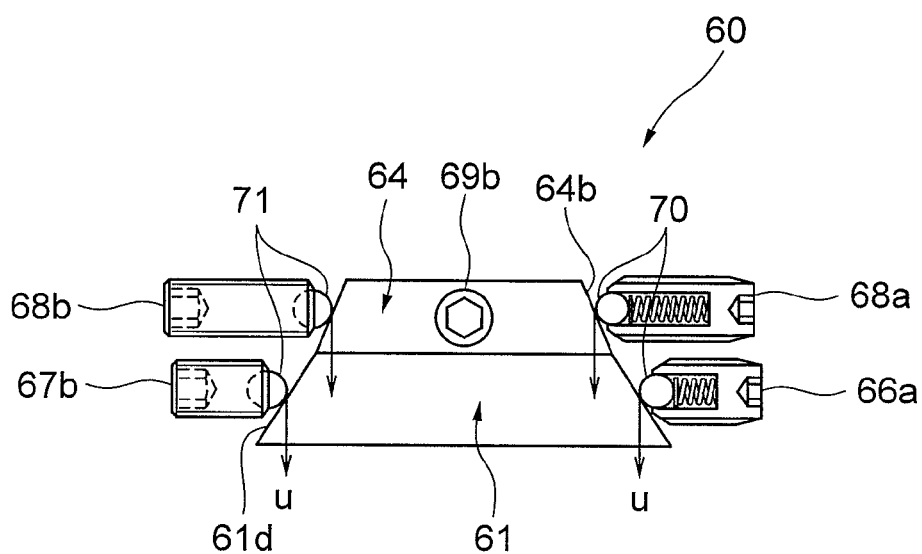
[FIG. 16B] A schematic diagram of the sample board and the sample holder in FIG. 16A as viewed from upward (on the side of the objective lens).
Figure 17A:
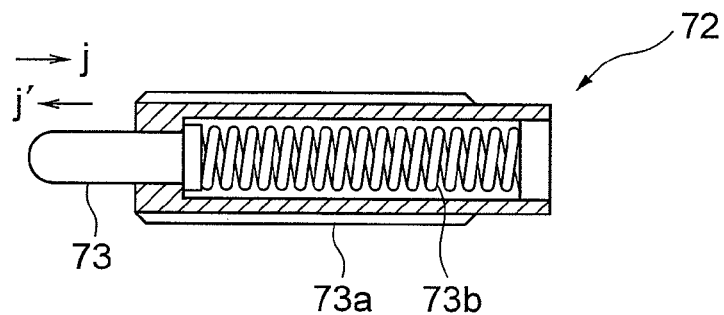
[FIG. 17A] A side sectional view of a spring plunger applicable to the alignment mechanism of the sample board and to the position adjusting mechanism of the sample holder in FIG. 12.
Figure 17B:
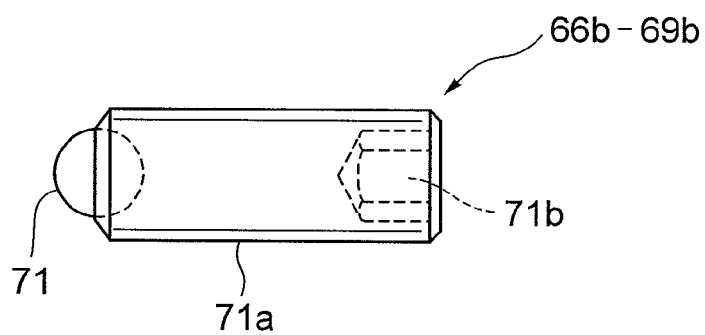
[FIG. 17B] A side view of an adjusting screw applicable to the alignment mechanism of the sample board and to the position adjusting mechanism of the sample holder in FIG. 12.

FIG. 16A is a schematic diagram illustrating the sample board and the sample holder in FIG. 12 as viewed from upward (on the side of the objective lens) for explaining an alignment mechanism of the sample board and a position adjusting mechanism of the sample holder in FIG. 12, FIG. 16B is a schematic diagram as viewed from the side surface. FIG. 17A is a side sectional view of a spring plunger applicable to the alignment mechanism of the sample board and to the position adjusting mechanism of the sample holder in FIG. 12, FIG. 17B is a side view of an adjusting screw, and FIG. 17C is a side sectional view of a ball plunger.

The sample board 61 is formed with the pinhole structure as in FIGS. 11B, 14A and 14B and therefore requires alignment between the position of the pinhole 61a and an optical axis of the objective lens 8a when observed, and, for attaining this alignment, the sample board 61 of the sample fitting portion 60 is provided with the alignment mechanism.

Namely, as in FIGS. 16A and 16B, the alignment mechanism of the sample board 61 is that the ball plunger 66a with the spring and the adjusting screw 66b are disposed in extension in the horizontal direction in the Figures in a way that faces each other with the central pinhole 61a interposed therebetween, then balls 70 provided at front edges thereof abut on the inclined surface 61d of the sample board 61, further another couple of the ball plunger 67a with the spring and the adjusting screw 67b are disposed in extension in the horizontal direction in the Figures in a way that faces each other with the central pinhole 61a interposed therebetween, and the balls 71 provided at the front edges thereof abut on the inclined surface 61d of the sample board 61.

Figure 17C:
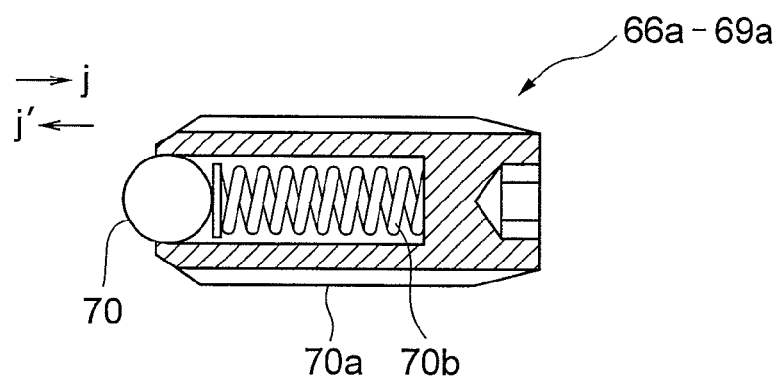
[FIG. 17C] A side sectional view of a ball plunger applicable to the alignment mechanism of the sample board and to the position adjusting mechanism of the sample holder in FIG. 12.

In each of the ball plungers 66a, 67a, as in FIG. 17C, the outer peripheral surface 70a thereof is formed with the screw, and a built-in coil spring 70b is extended in a longitudinal direction within an internal cavity. Each of the ball plungers 66a, 67a, as in FIGS. 16A and 16B, is screwed into the screw hole 16f (FIG. 13A) of the fixation component 16 from the outer peripheral surface 70a so that the ball 70 at the front edge abuts on the inclined surface 61d of the sample board 61 and is pressed in a direction j, at which time the coil spring 70b is compressed, and the ball 70 abuts on the inclined surface 61d while the resilient force of the spring applies biasing force in an opposite direction j'.

Further, each of the adjusting screws 66b, 67b, of which the outer peripheral surface 71a is formed with the screw as in FIG. 17B, is screwed into the screw hole 16g (FIG. 13A) of the fixation component 16 from the outer peripheral surface 71a so that the ball 71 at the front edge abuts on the inclined surface 61d of the sample board 61.

As in FIG. 16A, the ball plunger 66a and the adjusting screw 66b are disposed on a straight line s extending via the central pinhole 61a, further another couple of the ball plunger 67a and the adjusting screw 67b are disposed on a straight line t orthogonal to the straight line s via the central pinhole 61a, and the adjusting screws 66b, 67b are rotationally moved on the straight lines s, t by use of a hexagonal bolt hole 71b on the rear surface, thereby enabling the sample board 61 to be positioned in the biaxial directions.

The pinhole 61a of the sample board 61 is positionally adjusted so as to be positioned at the center of a field of view while observing the microscope image by sliding the sample board 61 in the horizontal direction w and in the vertical direction on the sheet surface with the rotation of the adjusting screws 66b, 67b, thereby completing the positioning (alignment) between the pinhole 61a and the optical axis k of the objective lens 8a.

As described above, the sample board 61 is housed within the fixation component 16 which holds the objective lens 8a, and is fixed in a way that enables the sample board 61 to be positioned from the biaxial directions by combining the spring-type plungers 66a, 67a screwed into the fixation component 16 with the positioning adjustment screws 66b, 67b. At this time, since the outer diametrical surface of the sample board 61 is the inclined surface 61d, as in FIG. 16B, when receiving the positioning stress from the horizontal direction illustrated in the Figure by dint of the biasing force of each of the ball plungers 66a, 67a toward the direction j' (FIG. 17C), a component of downward u occurs at each stress point, then a component force of the downward u prevents the sample board 61 from being inclined as well as enabling the fixation of the sample board 61 to be stabilized, and the sample board 61 can be prevented from being shifted in position even under the centrifugal excessive gravity.

Next, the position adjusting mechanism of the sample holder 64 will be described. The sample holder 64 is placed on the sample board 61 and can be, in the same way as in the alignment mechanism of the sample board 61, fixed in the positioning-enabled manner.

Namely, the position adjusting mechanism of the sample holder 64 is, as in FIGS. 16A and 16B, configured such that the ball plunger 68a with the spring and the adjusting screw 68b are disposed in extension in the horizontal in the Figures in a way that faces each other with the center interposed therebetween, then balls 70 provided at front edges thereof abut on the inclined surface 64d of the sample holder 64, further another couple of the ball plunger 69a with the spring and the adjusting screw 69b are disposed in extension in the horizontal in the Figures in a way that faces each other with the center interposed therebetween, then balls 71 provided at front edges thereof abut on the inclined surface 64b of the sample holder 64.

Each of the ball plungers 68a, 69a has the same configuration as in FIG. 17C, is screwed into the screw hole 16f (FIG. 13A) of the fixation component 16 from the outer peripheral surface 70a so that the ball 70 at the front edge abuts on the inclined surface 64d of the sample holder 64 and is pressed in a direction j, at which time the coil spring 70b is compressed, and the ball 70 abuts on the inclined surface 64d while the resilient force of the spring applies the biasing force in the opposite direction j'.

Moreover, each of the adjusting screws 68b, 69b has the same configuration as in FIG. 17B, is screwed into the screw hole 16f (FIG. 13A) of the fixation component 16 from the outer peripheral surface 71a so that the ball 71 at the front edge abuts on the inclined surface 64b of the sample holder 64.

As in FIG. 16A, the ball plunger 68a and the adjusting screw 68b are disposed on a straight line g extending via the center, further another couple of the ball plunger 69a and the adjusting screw 69b are disposed on a straight line h orthogonal to the straight line g via the center, and the adjusting screws 68b, 69b are rotationally moved on the straight lines g, h, thereby enabling the sample holder 64 to be positioned in the biaxial directions.

The position of the sample holder 64 is adjusted with respect to the optical axis k of the objective lens 8a by sliding the sample holder 64 in the horizontal direction w and in the direction vertical direction on the sheet surface in FIG. 15C with the rotation of the adjusting screws 68b, 69b, whereby the observation region within the reactor 6 can be adjusted by adjusting the position of the reactor 6 within the sample holder 64.

As described above, the sample holder 64 is fixed in a way that enables the sample holder 64 to be positioned from the biaxial directions by combining the spring-type plungers 68a, 69a screwed into the fixation component 16 with the positioning adjustment screws 68b, 69b. With this contrivance, since the outer diametrical surface of the sample holder 64 is the inclined surface 64d, as in FIG. 16B, when receiving the positioning stress from the horizontal direction illustrated in the Figure by dint of the biasing force of each of the ball plungers 68a, 69a toward the direction j' (FIG. 17C), the component of the downward u occurs at each stress point, then the component force of the downward u prevents the sample holder 64 from being inclined as well as enabling the fixation of the sample holder 64 to be stabilized, and the sample holder 64 can be prevented from being shifted in position even under the centrifugal excessive gravity.

The spring plunger 72 as depicted in FIG. 17A may also be employed for the ball plungers 66a to 69a used for the alignment mechanism and the position adjusting mechanism described above. Namely, the spring plunger 72 in FIG. 17A is formed with the screw on an outer peripheral surface 73a and has a built-in coil spring 73b extending in the longitudinal direction of the internal cavity. The spring plunger 72 is, as illustrated in FIGS. 16A and 16B, screwed into the screw holes 16f, 16g (FIG. 13A) of the fixation component 16 from the outer peripheral surface 73a so that a shaft 73 having a curved-surface at its front edge abuts on the inclined surface 61d of the sample board 61 and the inclined surface 64b of the sample holder 64, and is pressed in the direction j, at which time the coil spring 73b is compressed, and the shaft 73 abuts on the inclined surfaces 61d, 64b while the resilient force of the spring applies the biasing force in the opposite direction j'.

Furthermore, as in FIG. 16A, when the centrifugal force F is applied to the sample fitting portion 60 by dint of the rotation of the rotary disc 4 of the observable centrifugal apparatus A, it is preferable that the respective plungers 66a to 69a of the alignment mechanism and the position adjusting mechanism be disposed in the positions that are hard to be affected by the centrifugal force F.

The third embodiment involves using, for further improving the magnification and the resolution, SLMPL50x (which is 0.45 in numerical aperture (NA), 15.0 mm in working distance and 91 g in mass) made by Olympus Corporation for the objective lens 8a, and STC-172C (which has 400,000 pixels and is 0.13Lux at F1.2 in minimum object illuminance) made by Sensor Technology co., Ltd. for the imaging device (camera).

As described above, according to the third embodiment, the backlight illumination beams penetrate the pinhole 61a of the sample board 61 and irradiate over almost only the observation region 6a of the observation object with the result that the image contrast is improved, the image with the high resolution is acquired, and the observation at the high-magnification can be attained, whereby more minute object than the minute organism and the micro beads of polystyrene, e.g., the minute organ (e.g., starch grains called amyloplast) within a plant cell on the order of several μm or under, can be observed.

EXAMPLES

Next, the present invention will be discussed by way of examples more specifically but is not limited to these examples.

First Example

A first example is that the observable centrifugal apparatus A is utilized for selecting a size of the polystyrene beads.

Figure 7:
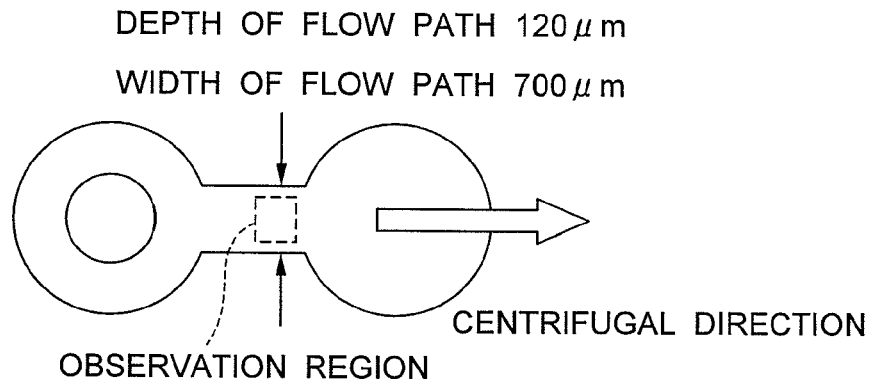
[FIG. 7] A plan view schematically illustrating a flow path pattern of a flow path forming chip used in a first example.

A flow path device formed with a dumbbell-shaped hyperfine flow path pattern (which is a flow path taking such a configuration that circular solution vessels are provided at both side ends and connected to each other via a straight flow path) as depicted in FIG. 7 is manufactured as the reactor 6, and is installed in the observable centrifugal apparatus A, in which a solution of the polystyrene beads having different sizes is introduced on a decentrifugal side in a state where the flow path device is filled with the solution, and a velocity, at which the beads pass through the flow path by dint of the centrifugal force, is measured.

The flow path device has a structure that a PDMS (polydimethylsiloxane) resin formed with the hyperfine flow path pattern as in FIG. 7 is pasted onto a glass substrate. The flow path pattern takes a shape that the circular solution vessels each having a diameter of 3 mm are connected to each other via the straight flow path having a width of 700 μm, and a depth of the flow path is approximately 120 μm. One side of the solution vessel is holed for introducing the solution, and the solution of the beads can be introduced via this hole.

The flow path device is fitted to the observable centrifugal apparatus A so that the straight flow path portion can be observed through the CCD camera 10 with the solution introducing hole being directed toward the decentrifugal side. At this time, the interior of the flow path is filled with a test solution (0.1 M mannitol aqueous solution). The polystyrene solution is introduced via the solution introducing hole, and, when driving the observable centrifugal apparatus A, the polystyrene beads move to the solution vessel on the centrifugal side via the straight flow path by dint of the centrifugal force. In the observable centrifugal apparatus A, the velocity at which the polystyrene beads move within the straight flow path can be measured with an optional number of rotation (the centrifugal force), and hence the moving velocity of the polystyrene beads can be precisely measured.

Figure 8:
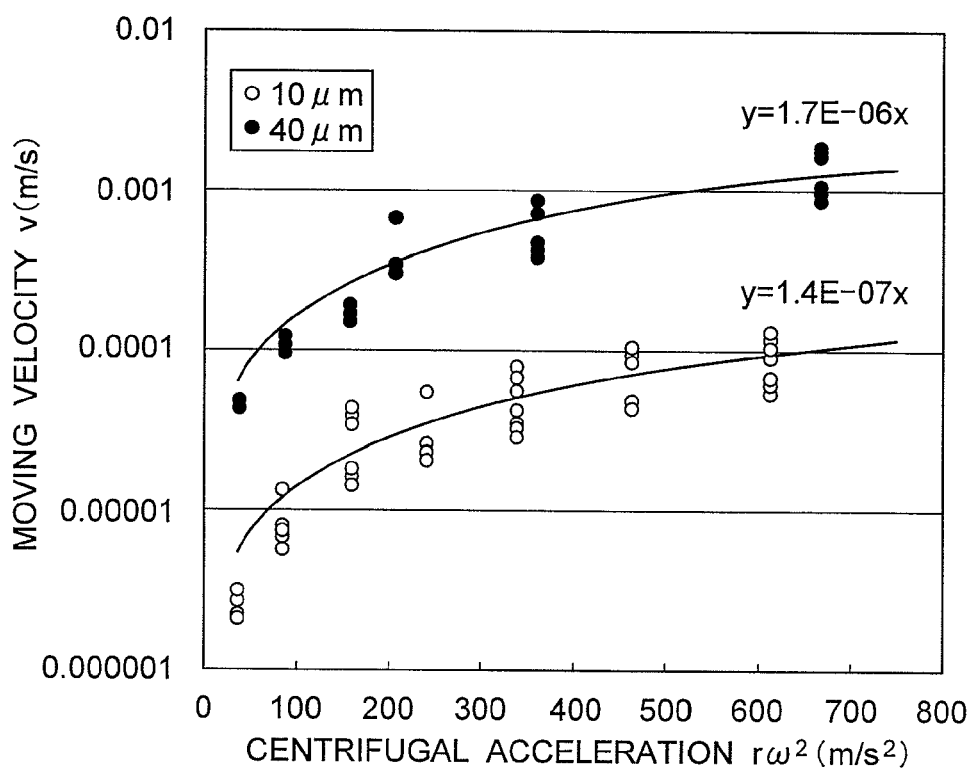
[FIG. 8] A graph illustrating a relationship between a centrifugal acceleration and a moving velocity when polystyrene beads having different diameters move in a straight flow path in the first example.

The polystyrene beads (4000 Series Moritex Corp.) having a diameter of 10 μm and a diameter of 40 μm are used as the sample, and a difference between the moving (sedimentation) velocity under the respective centrifugal forces is measured. FIG. 8 illustrates measured results thereof. As understood from FIG. 8, it is demonstrated that the beads having the larger diameter show the higher moving velocity, and the size can be selected while observing the behavior of each bead.

Second Example

Figure 9:
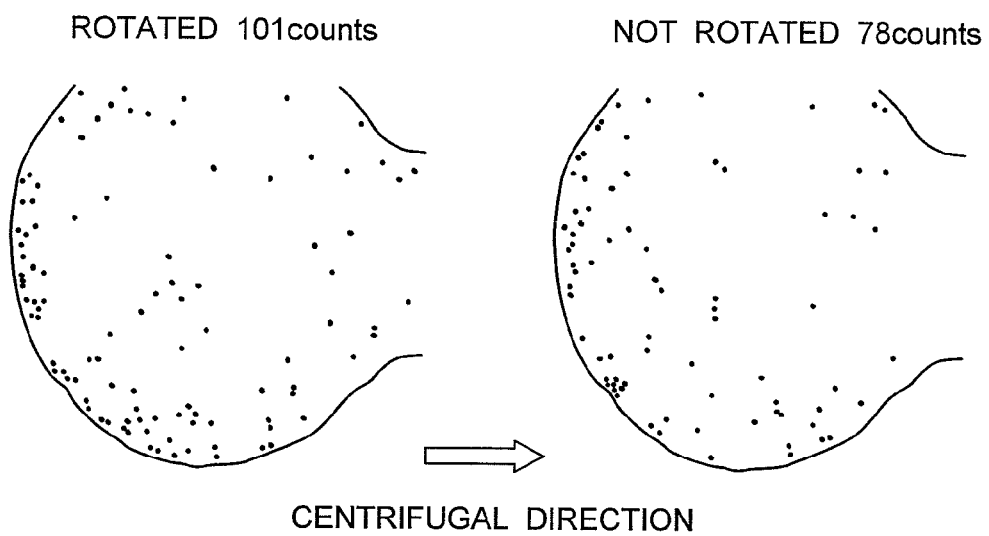
[FIG. 9] A diagram illustrating an occurrence probability of paramecium in a solution vessel on a decentrifugal side in the case of applying a load of the centrifugal force by rotating the flow path device and in the case of applying none of the load of the centrifugal force without any rotation in a second example.

A second example is that the observable centrifugal apparatus A described above measures the geotactic behavior of the minute organism. To be specific, in the second example, paramecium is introduced into the solution vessel on the centrifugal side of the dumbbell-shaped flow path device in FIG. 7, and the geotactic behavior is observed. As a result, according to the second example in which a load of the centrifugal force is applied by making the rotation, as in FIG. 9, an occurrence probability of the paramecium in the solution vessel on the decentrifugal side increases by approximately 30% as compared with a case of applying the load of the centrifugal force without any rotation.

As given above, the best mode for carrying out the present invention and the examples thereof have been discussed above, however, the present invention is not limited to the best mode and the examples and can be modified in a variety of forms within the scope of the technical idea of the present invention.

INDUSTRIAL APPLICABILITY

As described above, the observable centrifugal apparatus according to the present invention is capable of checking in real time the state of the sample in the reaction process of the separation or the synthesization through the image with the stable image quality at the high frame rate (the number of frames), and is useful as the apparatus capable of further improving the magnification and the resolution. Moreover, the observation apparatus is useful as the apparatus capable of further improving the magnification and the resolution.

What is claimed is:

1. An observable centrifugal apparatus comprising:
a rotary disc which rotates;
a reactor which is disposed on said rotary disc and rotates together with said rotary disc while housing a sample; and
a microscope for observing a state of the sample within said reactor by recognizing the state of the sample,
said observable centrifugal apparatus separating or reacting predetermined substances from the sample within said reactor by applying a centrifugal force to said sample,
wherein said microscope, an imaging device for photographing a microscope image of the sample state within said reactor, caught by said microscope, and an image transmission device for transmitting the photographed image of the microscope image photographed by said imaging device as a dynamic image, are positioned in the center of rotation of said rotary disc and/or in the vicinity of the center of rotation.

2. An observable centrifugal apparatus according to claim 1, wherein a light path of said microscope is partially, within a lens barrel, refracted at a predetermined angle to a disc surface of said rotary disc, and said imaging device is positioned in the vicinity of the center of rotation of said rotary disc so that the microscope image can be photographed on the light path of said microscope, which is refracted at the predetermined angle.

3. An observable centrifugal apparatus according to claim 2, wherein an objective lens of said microscope and said reactor are integrally fixed to said rotary disc through the same component, and relative displacement between said objective lens and said reactor due to the rotational vibrations is minimized.

4. An observable centrifugal apparatus according to claim 3, further comprising a sample fitting portion to which said reactor is fitted,
wherein said sample fitting portion includes a pinhole for condensing, and a sample board which supports said reactor.

5. An observable centrifugal apparatus according to claim 1, wherein said image transmission device includes an image wireless transmission device for wirelessly transmitting in real time the photographed image of the microscope image photographed by said imaging device as a dynamic image.

6. An observable centrifugal apparatus according to claim 1, wherein said rotary disc is rotationally driven by a motor of build-in type.

7. An observable centrifugal apparatus according to claim 5, wherein said image wireless transmission device converts data of the photographed image of the microscope image photographed by said imaging device into non-compressed digital signals, and wirelessly transmits the digital signals to an external receiving device.

8. An observable centrifugal apparatus according to claim 1, further comprising an illumination apparatus performing backlight illumination over the sample within said reactor.

9. An observable centrifugal apparatus according to claim 1, further comprising an epi-illumination apparatus performing epi-illumination over the sample within said reactor.

10. An observable centrifugal apparatus according to claim 1, wherein a rotary shaft of said rotary disc is rotatably supported by an air bearing kept in a non-contact state with respect to said rotary shaft by dint of blast air.

11. An observable centrifugal apparatus according to claim 1, wherein said sample fitting portion includes an alignment mechanism for adjusting a relative position between an optical axis of the objective lens of said microscope and the pinhole of said sample board.

12. An observable centrifugal apparatus according to claim 5, wherein said sample fitting portion includes a sample holder which holds said reactor on said sample board, and a position adjusting mechanism for adjusting a relative position between the optical axis of the objective lens of said microscope and said reactor held by said sample holder.

13. An observable centrifugal apparatus according to claim 12, wherein said sample fitting portion is provided within a fixation component which fixes the objective lens of said microscope to said rotary disc, and
said sample board and said sample holder are fixed on the side of said rotary disc by said alignment mechanism, said position adjusting mechanism and said fixation component.

14. An observation apparatus comprising:
a microscope for observing an observation object;
a sample board which supports the observation object; and
an illumination apparatus which performs backlight illumination over the observation object,
wherein said sample board is formed with a pinhole,
the backlight illumination beams emitted from said illumination apparatus penetrate the pinhole and illuminate over the observation object supported on said sample board.

15. An observation apparatus according to claim 14, further comprising an alignment mechanism for adjusting a relative position between an optical axis of the objective lens of said microscope and the pinhole of said sample board.

16. An observation apparatus according to claim 14, further comprising a position adjusting mechanism for adjusting a relative position between the optical axis of the objective lens of said microscope and the observation object supported on said sample board.

* * * * *